US008567161B2

(12) United States Patent
Man et al.

(10) Patent No.: US 8,567,161 B2
(45) Date of Patent: Oct. 29, 2013

(54) WETTING AGENTS FOR ASEPTIC FILLING

(75) Inventors: Victor F. Man, St. Paul, MN (US); Janel M. Kieffer, Hastings, MN (US); Michael C. Denoma, Vadnais Heights, MN (US); Yvonne M. Killeen, South St. Paul, MN (US); Joshua P. Magnuson, St. Paul, MN (US)

(73) Assignee: Ecolab USA Inc., Saint Paul, MN (US)

( * ) Notice: Subject to any disclaimer, the term of this patent is extended or adjusted under 35 U.S.C. 154(b) by 600 days.

(21) Appl. No.: 12/778,711

(22) Filed: May 12, 2010

(65) Prior Publication Data
US 2010/0300044 A1  Dec. 2, 2010

Related U.S. Application Data

(60) Provisional application No. 61/181,836, filed on May 28, 2009.

(51) Int. Cl.
*B65B 55/02* (2006.01)
*B65B 55/10* (2006.01)

(52) U.S. Cl.
USPC ............................. 53/425; 53/426; 53/428

(58) Field of Classification Search
USPC ............................ 53/425, 426, 428
See application file for complete search history.

(56) References Cited

U.S. PATENT DOCUMENTS

| | | | |
|---|---|---|---|
| 3,734,798 A * | 5/1973 | Dooley | 53/478 |
| 3,789,569 A * | 2/1974 | Egger | 53/426 |
| 3,911,642 A * | 10/1975 | Ernstsson et al. | 53/426 |
| 4,426,362 A | 1/1984 | Copeland et al. | |
| 4,492,646 A | 1/1985 | Welch | |
| 4,618,914 A | 10/1986 | Sato et al. | |
| 4,647,258 A | 3/1987 | Massarsch | |
| 4,654,161 A | 3/1987 | Kollmeier et al. | |
| 4,687,121 A | 8/1987 | Copeland | |
| 4,690,305 A | 9/1987 | Copeland | |
| RE32,763 E | 10/1988 | Fernholtz et al. | |
| RE32,818 E | 1/1989 | Fernholz et al. | |

(Continued)

FOREIGN PATENT DOCUMENTS

| | | |
|---|---|---|
| DE | 69918694 T2 | 7/2005 |
| EP | 1102834 | 7/2004 |

(Continued)

OTHER PUBLICATIONS http://books.google.com/books?id=D3zqLtl-ch4C&pg=PA117&lpg=PA117&dq=R-O-(CH2CH2O)n-H&source=bl&ots=A3Ns5NmZrs&sig=mf4VxBljeKE55Pa2dGrL8yYE58k&hl=en&sa=X&ei=UyRbUMOfDoPX0QGftYHYAQ&ved=0CDMQ6AEwBTgK#v=onepage&q=R-O-(CH2CH2O)n-H&f=true; "Handbook of Surfactants", M. R. Porter; pp. 116-118;Sep. 30, 1994.*

(Continued)

*Primary Examiner* — Hemant M Desai
*Assistant Examiner* — Gloria R Weeks
(74) *Attorney, Agent, or Firm* — McKee, Voorhees & Sease, P.L.C.

(57) ABSTRACT

The present invention is directed to wetting agent compositions and methods for making and using the wetting agent compositions. The compositions of the invention include a sheeting agent, a defoaming agent, and an association disruption agent. The wetting agent compositions of the present invention result in a faster draining/drying time on most substrates compared to conventional wetting agents. The wetting agent compositions of the present invention are especially suitable for use on plastic substrates.

19 Claims, 9 Drawing Sheets

(56) References Cited

U.S. PATENT DOCUMENTS

| | | | |
|---|---|---|---|
| 4,826,661 A | 5/1989 | Copeland et al. | |
| 4,830,773 A | 5/1989 | Olson | |
| 5,273,677 A | 12/1993 | Arif | |
| 5,358,653 A | 10/1994 | Gladfelter et al. | |
| 5,397,506 A | 3/1995 | Groth et al. | |
| 5,474,698 A | 12/1995 | Rolando et al. | |
| 5,501,815 A | 3/1996 | Man | |
| 5,585,129 A * | 12/1996 | Geddes et al. | 426/394 |
| 5,589,099 A | 12/1996 | Baum | |
| 5,603,776 A | 2/1997 | Lentsch et al. | |
| 5,674,831 A | 10/1997 | Schulz et al. | |
| 5,874,164 A * | 2/1999 | Caldwell | 428/306.6 |
| 5,876,514 A | 3/1999 | Rolando et al. | |
| 5,880,088 A | 3/1999 | Lentsch et al. | |
| 5,880,089 A | 3/1999 | Lentsch et al. | |
| H1818 H | 11/1999 | Potgieter et al. | |
| 6,040,251 A * | 3/2000 | Caldwell | 442/123 |
| 6,258,765 B1 | 7/2001 | Wei et al. | |
| 6,294,515 B1 | 9/2001 | Baum | |
| 6,302,968 B1 * | 10/2001 | Baum et al. | 134/30 |
| 6,479,044 B1 * | 11/2002 | Mahieu et al. | 424/78.03 |
| 6,530,383 B1 | 3/2003 | Rogmann et al. | |
| 6,534,075 B1 * | 3/2003 | Hei et al. | 424/405 |
| 6,537,961 B1 | 3/2003 | Koch | |
| 6,569,506 B1 * | 5/2003 | Jerdee et al. | 428/35.7 |
| RE38,262 E | 10/2003 | Rolando et al. | |
| 6,808,691 B1 * | 10/2004 | Herve et al. | 422/294 |
| 6,927,237 B2 * | 8/2005 | Hei et al. | 514/557 |
| 6,956,019 B2 | 10/2005 | Lentsch et al. | |
| 7,279,455 B2 | 10/2007 | Kieffer et al. | |
| 7,341,983 B2 * | 3/2008 | Pedersen et al. | 510/383 |
| 7,592,301 B2 | 9/2009 | Smith et al. | |
| 7,954,306 B2 * | 6/2011 | Gould | 53/452 |
| 2002/0058601 A1 * | 5/2002 | Jordan | 510/421 |
| 2002/0106361 A1 * | 8/2002 | Poulsen et al. | 424/94.4 |
| 2002/0192340 A1 | 12/2002 | Swart et al. | |
| 2003/0109403 A1 | 6/2003 | Man et al. | |
| 2003/0166494 A1 | 9/2003 | Man et al. | |
| 2003/0203991 A1 * | 10/2003 | Schottman et al. | 523/334 |
| 2004/0033269 A1 | 2/2004 | Hei et al. | |
| 2004/0110657 A1 | 6/2004 | Strothoff | |
| 2004/0157051 A1 * | 8/2004 | Trent et al. | 428/327 |
| 2004/0157760 A1 | 8/2004 | Man et al. | |
| 2004/0175407 A1 * | 9/2004 | McDaniel | 424/423 |
| 2005/0101516 A1 | 5/2005 | Kieffer et al. | |
| 2005/0130865 A1 | 6/2005 | Schmid et al. | |
| 2005/0143280 A1 | 6/2005 | Nelson et al. | |
| 2006/0058209 A1 | 3/2006 | Lentsch et al. | |
| 2006/0189508 A1 | 8/2006 | Brooker et al. | |
| 2006/0246242 A1 | 11/2006 | Siegel et al. | |
| 2007/0253926 A1 | 11/2007 | Tadrowski et al. | |
| 2008/0293615 A1 | 11/2008 | Kieffer et al. | |
| 2009/0035339 A1 | 2/2009 | Istvan et al. | |
| 2009/0194450 A1 * | 8/2009 | Dabadie et al. | 206/484 |
| 2009/0196897 A1 | 8/2009 | Gladfelter et al. | |
| 2010/0009886 A1 | 1/2010 | Smith et al. | |
| 2010/0062130 A1 * | 3/2010 | Finley et al. | 426/531 |
| 2010/0178401 A1 * | 7/2010 | Van Appeldoorn et al. | 426/392 |
| 2010/0300044 A1 | 12/2010 | Man et al. | |

FOREIGN PATENT DOCUMENTS

| | | |
|---|---|---|
| JP | 2009111294 | 5/2009 |
| WO | WO89/11525 | 11/1989 |
| WO | WO00/08125 | 2/2000 |
| WO | WO 00/46327 A1 | 8/2000 |
| WO | WO 01/83879 A1 | 11/2001 |
| WO | WO2005/085321 | 9/2005 |

OTHER PUBLICATIONS

BASF Corporation Technical Bulletin, "Plurafac LF-221 Alcohol Alkoxylate", 2002 BASF Corporation, Mount Olive, New Jersey (1 page).

Dow Personal Care, "Kathon CG, A Safe, Effective, Globally Approved Preservative for Rinse-Off Products", Rohm and Haas, 2007 (9 pages).

* cited by examiner

WETTING AGENTS FOR ASEPTIC FILLING

RELATED APPLICATIONS

This application claims priority to U.S. Provisional Application Ser. No. 61/181,836, filed on May 28, 2009, and entitled "Wetting Agents for Aseptic Filling." The entire contents of this patent application is hereby expressly incorporated herein by reference including, without limitation, the specification, claims and abstract, as well as any figures, tables, or drawings thereof.

This application is also related to U.S. Provisional Application Ser. No. 61/177,444, filed on May 12, 2009, and U.S. Utility Application Ser. No. 12/778,683 filed concurrently herewith, and both entitled "Fast Drying and Fast Draining Rinse Aid." The entire contents of these patent applications are hereby expressly incorporated herein by reference including, without limitation, the specification, claims and abstract, as well as any figures, tables, or drawings thereof.

FIELD OF INVENTION

The present invention relates to wetting agent compositions, and methods for manufacturing and using the wetting agent compositions. The wetting agent compositions generally include a sheeting agent, a defoaming agent, and one or more of an association disruption agent. The wetting agents can be used in aqueous solutions on articles including, for example, cookware, dishware, flatware, glasses, cups, hard surfaces, glass surfaces, vehicle surfaces, etc. The wetting agents are especially effective on plastic surfaces. The wetting agents can also be used as wetting agents for use in aseptic filling procedures.

BACKGROUND

Wetting agents are used in a variety of applications to lower the surface tension of water to allow a solution to wet surfaces more effectively. Wetting agents are included in numerous compositions including, but not limited to, cleaning solutions, antimicrobial solutions, paints, adhesives, and inks. A number of wetting agents are currently known, each having certain advantages and disadvantages. There is an ongoing need for alternative wetting agent compositions.

SUMMARY

In some aspects, the present invention relates to methods for aseptic packaging of food, beverages or pharmaceuticals. The methods comprise contacting a package with a composition consisting essentially of a wetting agent, and an antimicrobial agent. The wetting agent consists essentially of a sheeting agent, a defoaming agent, one or more of an association disruption agent; and an additional ingredient selected from the group consisting of a carrier, a hydrotrope, a chelating/sequestering agent, and combinations thereof. The methods also include filling the package with a substance selected from the group consisting of food, beverage, pharmaceutical, and combinations thereof and sealing the package.

In some embodiments, the step of contacting comprises applying the composition to the packaging for an amount of time sufficient to reduce a microorganism population present on the package. In other embodiments, the composition is applied to the packaging for at least 3 seconds. In yet other embodiments, the step of contacting comprises applying the composition to the packaging at a temperature of between about 0° C. and about 100° C.

In some embodiments, the sheeting agent comprises at least one compound having the structure represented by formula I:

$$R-O-(CH_2CH_2O)_n-H \qquad (I)$$

wherein R is a ($C_1$-$C_{12}$) alkyl group, and n is an integer in the range of 1 to 100. In some embodiments, n is an integer in the range of 15 to 30. In other embodiments, n is 21.

In some embodiments, the defoaming agent comprises a polymer compound including one or more ethylene oxide groups. In still yet other embodiments, the defoaming agent comprises a polyether compound prepared from ethylene oxide, propylene oxide, or a mixture thereof. In other embodiments, the defoaming agent comprises a polyoxypropylene-polyoxyethylene block copolymer surfactant. In still yet other embodiments, the one or more association disruption agent comprises an alcohol alkoxylate. In some embodiments, the alkoxylate portion of the association disruption agent is selected from the group consisting of ethylene oxides, propylene oxides, butylene oxides, pentalene oxides, hexylene oxides, heptalene oxides, octalene oxides, nonalene oxides, decylene oxides, and mixtures and derivatives thereof. In some embodiments, the composition comprises at least two association disruption agents. In other embodiments, the composition comprises at least three association disruption agents.

In some embodiments, the ratio of sheeting agent to defoaming agent to association disrupting agent is about 1.0:1.5:30 to about 1:2:1. In other embodiments, the association disruption agent is present at an amount effective to reduce the contact angle of the composition by between about 5° to about 15°. In still yet other embodiments, the antimicrobial agent is selected from the group consisting of a peroxygen compound, a percarboxylic acid, a monoester of a dicarboxylic acid, a diester of a dicarboxylic acid, and mixtures thereof.

In some embodiments, the wetting agent is present in the composition at an amount of from about 20 ppm to about 2000 ppm. In other embodiments, the method further comprises a rinse step between the step of contacting the package with the composition, and filling the package with a substance.

In some aspects, the present invention provides a wetting agent composition consisting essentially of a sheeting agent, a defoaming agent, at least one of an association disruption agent, and an additional ingredient selected from the group consisting of a carrier, a hydrotrope, a chelating/sequestering agent, and combinations thereof.

In other aspects, the present invention provides a composition consisting essentially of a wetting agent composition consisting essentially of a sheeting agent, a defoaming agent, at least one of an association disruption agent, an additional ingredient selected from the group consisting of a carrier, a hydrotrope, a chelating/sequestering agent, and combinations thereof, and an antimicrobial agent.

In some aspects, the present invention relates to a method for aseptic packaging. The method comprises forming an aseptic packaging use solution, contacting a package with the aseptic packaging use solution, filling the package with a substance selected from the group consisting of food, beverage, pharmaceutical, and combinations thereof, and sealing the package.

In some embodiments, the step of forming an aseptic packaging use solution comprises diluting a composition to a use concentration of between about 0.01 wt % to about 10 wt %, wherein the composition consists essentially of a wetting agent and an antimicrobial agent. In other embodiments, the wetting agent consists essentially of a sheeting agent, a defoaming agent, at least one association disruption agent, and an additional ingredient selected from the group consisting of a carrier, a hydrotrope, a chelating/sequestering agent, and combinations thereof. In some embodiments, the antimicrobial agent is selected from the group consisting of a peroxygen compound, a percarboxylic acid, a monoester of a dicarboxylic acid, a diester of a dicarboxylic acid, and mixtures thereof.

DETAILED DESCRIPTION

Figure 1:
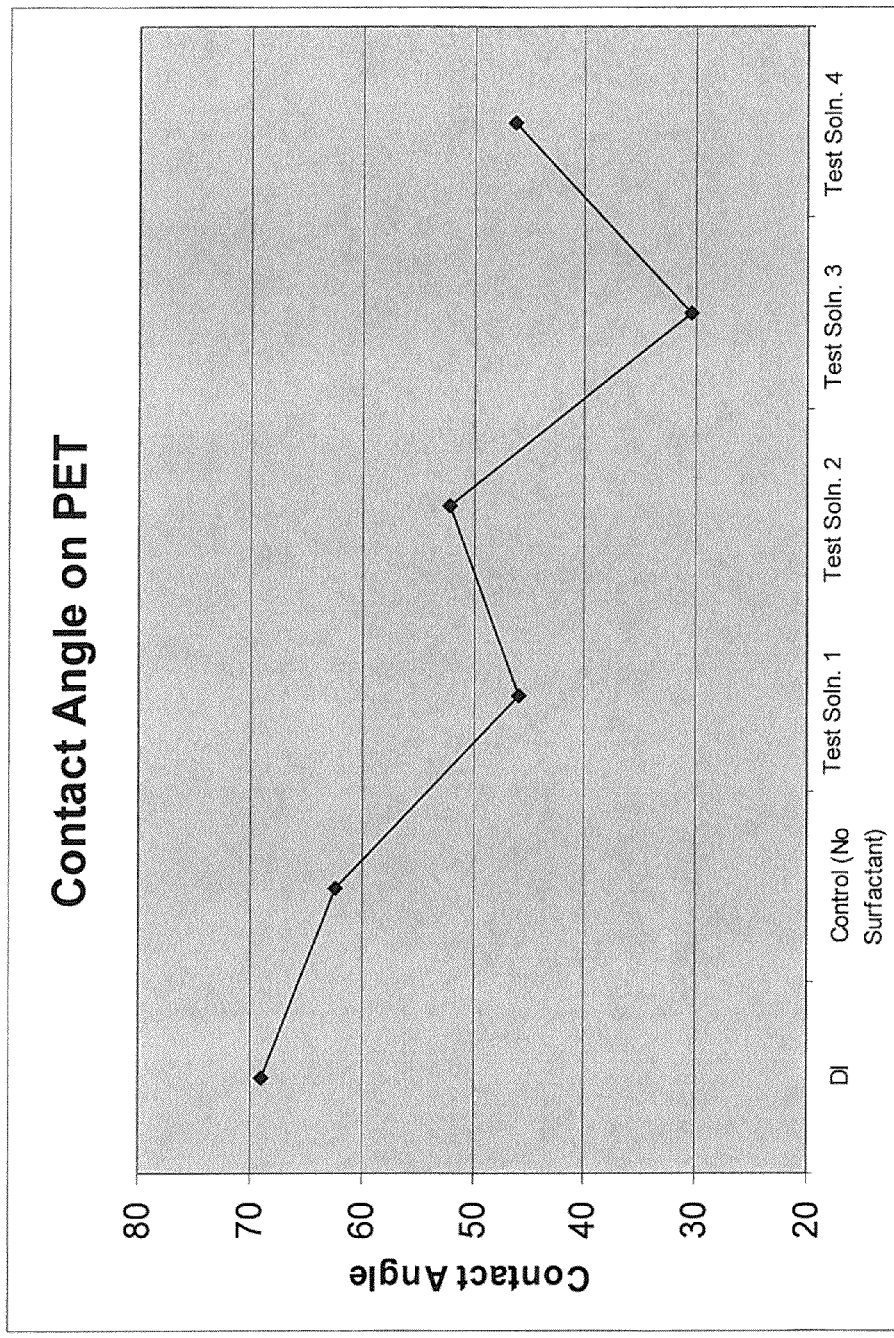
FIG. 1 is a graphical depiction of the average contact angle of various test solutions as described in Example 2.

The present invention relates to wetting agent compositions, and methods for making and using the wetting agent compositions. The wetting agents are especially effective when used in packaging processes, e.g., aseptic packaging/filling. In some aspects, the present invention provides wetting agent compositions including a sheeting agent, a defoaming agent, and one or more of an association disruption agent. It has been found that the combination of a sheeting agent, a defoaming agent, and one or more association disruption agent acts synergistically to produce low foaming wetting agent compositions with a moderately low viscoelasticity and increased wetting properties. Further, the compositions of the present invention have increased drying and draining times.

The wetting agents can be used in combination with one or more antimicrobial agents. The compositions of the invention can be used as wetting agents in a variety of applications, e.g., aseptic packaging/filling, pharmaceutical packaging, clean-in-place (CIP) or clean-out-of-place (COP) systems. So that the invention may be understood more clearly, certain terms are first defined.

As used herein, the term "antiredeposition agent" refers to a compound that helps keep a soil composition suspended in water instead of redepositing onto the object being cleaned.

As used herein, the term "ware" refers to items such as eating, cooking, and serving utensils. Exemplary items of ware include, but are not limited to: dishes, e.g., plates and bowls; eating utensils, e.g., forks, knives, and spoons; cups and glasses, e.g., drinking cups and glasses; serving dishes, e.g., fiberglass trays, insulated plate covers. As used herein, the term "warewashing" refers to washing, cleaning, or rinsing ware. The items of ware that can be contacted, e.g., washed, or rinsed, with the compositions of the invention can be made of any material. For example, ware includes items made of wood, metal, ceramics, glass, etc. Ware also refers to items made of plastic. Types of plastics that can be cleaned or rinsed with the compositions according to the invention include but are not limited to, those that include polycarbonate polymers (PC), acrilonitrile-butadiene-styrene polymers (ABS), and polysulfone polymers (PS). Another exemplary plastic that can be cleaned using the methods and compositions of the invention include polyethylene terephthalate (PET).

As used herein, the term "hard surface" includes showers, sinks, toilets, bathtubs, countertops, windows, mirrors, transportation vehicles, floors, and the like.

As used herein, the phrase "health care surface" refers to a surface of an instrument, a device, a cart, a cage, furniture, a structure, a building, or the like that is employed as part of a health care activity. Examples of health care surfaces include surfaces of medical or dental instruments, of medical or dental devices, of autoclaves and sterilizers, of electronic apparatus employed for monitoring patient health, and of floors, walls, or fixtures of structures in which health care occurs. Health care surfaces are found in hospital, surgical, infirmity, birthing, mortuary, and clinical diagnosis rooms. These surfaces can be those typified as "hard surfaces" (such as walls, floors, bed-pans, etc.,), or fabric surfaces, e.g., knit, woven, and non-woven surfaces (such as surgical garments, draperies, bed linens, bandages, etc.,), or patient-care equipment (such as respirators, diagnostic equipment, shunts, body scopes, wheel chairs, beds, etc.,), or surgical and diagnostic equipment. Health care surfaces include articles and surfaces employed in animal health care.

As used herein, the term "instrument" refers to the various medical or dental instruments or devices that can benefit from cleaning using water treated according to the methods of the present invention.

As used herein, the phrases "medical instrument," "dental instrument," "medical device," "dental device," "medical equipment," or "dental equipment" refer to instruments, devices, tools, appliances, apparatus, and equipment used in medicine or dentistry. Such instruments, devices, and equipment can be cold sterilized, soaked or washed and then heat sterilized, or otherwise benefit from cleaning using water treated according to the present invention. These various instruments, devices and equipment include, but are not limited to: diagnostic instruments, trays, pans, holders, racks, forceps, scissors, shears, saws (e.g. bone saws and their blades), hemostats, knives, chisels, rongeurs, files, nippers, drills, drill bits, rasps, burrs, spreaders, breakers, elevators, clamps, needle holders, carriers, clips, hooks, gouges, curettes, retractors, straightener, punches, extractors, scoops, keratomes, spatulas, expressors, trocars, dilators, cages, glassware, tubing, catheters, cannulas, plugs, stents, scopes (e.g., endoscopes, stethoscopes, and arthoscopes) and related equipment, and the like, or combinations thereof.

By the term "solid" as used to describe a composition of the present invention, it is meant that the hardened composition will not flow perceptibly and will substantially retain its shape under moderate stress or pressure or mere gravity, as for example, the shape of a mold when removed from the mold, the shape of an article as formed upon extrusion from an extruder, and the like. The degree of hardness of the solid composition can range from that of a fused solid block which is relatively dense and hard, for example, like concrete, to a consistency characterized as being malleable and sponge-like, similar to caulking material.

The "cloud point" of a surfactant rinse or sheeting agent is defined as the temperature at which a 1 wt. % aqueous solution of the surfactant turns cloudy when warmed.

As used herein, the term "alkyl" refers to a straight or branched chain monovalent hydrocarbon radical optionally containing one or more heteroatomic substitutions independently selected from S, O, Si, or N. Alkyl groups generally include those with one to twenty atoms. Alkyl groups may be unsubstituted or substituted with those substituents that do not interfere with the specified function of the composition. Substituents include alkoxy, hydroxy, mercapto, amino, alkyl substituted amino, or halo, for example. Examples of "alkyl"

as used herein include, but are not limited to, methyl, ethyl, n-propyl, n-butyl, n-pentyl, isobutyl, and isopropyl, and the like. In addition, "alkyl" may include "alylenes", "alkenylenes", or "alkylynes".

As used herein, the term "alkylene" refers to a straight or branched chain divalent hydrocarbon radical optionally containing one or more heteroatomic substitutions independently selected from S, O, Si, or N. Alkylene groups generally include those with one to twenty atoms. Alkylene groups may be unsubstituted or substituted with those substituents that do not interfere with the specified function of the composition. Substituents include alkoxy, hydroxy, mercapto, amino, alkyl substituted amino, or halo, for example. Examples of "alkylene" as used herein include, but are not limited to, methylene, ethylene, propane-1,3-diyl, propane-1,2-diyl and the like.

As used herein, the term "alkenylene" refers to a straight or branched chain divalent hydrocarbon radical having one or more carbon—carbon double bonds and optionally containing one or more heteroatomic substitutions independently selected from S, O, Si, or N. Alkenylene groups generally include those with one to twenty atoms. Alkenylene groups may be unsubstituted or substituted with those substituents that do not interfere with the specified function of the composition. Substituents include alkoxy, hydroxy, mercapto, amino, alkyl substituted amino, or halo, for example. Examples of "alkenylene" as used herein include, but are not limited to, ethene-1,2-diyl, propene-1,3-diyl, and the like.

As used herein, the term "alkylyne" refers to a straight or branched chain divalent hydrocarbon radical having one or more carbon—carbon triple bonds and optionally containing one or more heteroatomic substitutions independently selected from S, O, Si, or N. Alkylyne groups generally include those with one to twenty atoms. Alkylyne groups may be unsubstituted or substituted with those substituents that do not interfere with the specified function of the composition. Substituents include alkoxy, hydroxy, mercapto, amino, alkyl substituted amino, or halo, for example.

As used herein, the term "alkoxy", refers to —O-alkyl groups wherein alkyl is as defined above.

As used herein, the term "halogen" or "halo" shall include iodine, bromine, chlorine and fluorine.

As used herein, the terms "mercapto" and "sulfhydryl" refer to the substituent —SH.

As used herein, the term "hydroxy" refers to the substituent —OH.

A used herein, the term "amino" refers to the substituent —NH$_2$.

As used herein, "weight percent (wt %)," "percent by weight," "% by weight," and the like are synonyms that refer to the concentration of a substance as the weight of that substance divided by the total weight of the composition and multiplied by 100.

The methods and compositions of the present invention can comprise, consist of, or consist essentially of the listed steps or ingredients. As used herein the term "consisting essentially of" shall be construed to mean including the listed ingredients or steps and such additional ingredients or steps which do not materially affect the basic and novel properties of the composition or method. In some embodiments, a composition in accordance with embodiments of the present invention that "consists essentially of" the recited ingredients does not include any additional ingredients that alter the basic and novel properties of the composition, e.g., the drying time, sheeting ability, spotting or filming properties of the composition.

As used herein, the term "about" modifying the quantity of an ingredient in the compositions of the invention or employed in the methods of the invention refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term about also encompasses amounts that differ due to different equilibrium conditions for a composition resulting from a particular initial mixture. Whether or not modified by the term "about," the claims include equivalents to the quantities.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Wetting Agent Compositions

In some aspects, the present invention provides compositions that can be used as wetting agents. The wetting agent compositions of the invention have been found to provide improved sheeting action on a variety of substrates compared to conventional wetting agents. The wetting agents of the present invention have also been found to increase the spreading and penetrating properties of other ingredients, e.g., antimicrobial agents. The wetting agents of the present invention are especially effective when used in aseptic filling use solutions.

The wetting agent compositions of the present invention include a sheeting agent, a defoaming agent, and one or more of an association disruption agent. The sheeting agents for use with the wetting agents of the present invention include surfactants which are prone to association, giving rise to a higher thin film viscoelasticity. That is, the sheeting agents yield a relatively high and stable foam, with a relatively slow drainage time. It has been found that these sheeting agents can be defoamed using relatively simple defoaming agents. Although included in the compositions of the present invention primarily to defoam the sheeting agents, the defoaming agents for use in the present invention can also contribute to the sheeting performance of the compositions of the present invention.

The wetting agent compositions of the present invention also include an association disruption agent. As used herein the terms "association disruption agent" or "association disrupting agent" refer to a class of surfactants capable of interrupting the association of the sheeting and defoaming agents included in the compositions of the present invention. Without wishing to be bound by any particular theory, it is thought that the association disruption agents aid in the drying/draining time of the wetting agent compositions from the contacted substrates. That is, it is thought that by interrupting or reducing the association of the other active components of the wetting agent, the association disruption agents decrease the drainage time of the wetting agent from a surface. Similar to the defoaming agents however, the association disruption agents can also contribute to the sheeting performance of the compositions of the present invention.

Sheeting Agents

In some aspects, the wetting agent compositions of the present invention include a sheeting agent. In some embodiments, the sheeting agent includes one or more alcohol ethoxylate compounds that include an alkyl group that has 12 or fewer carbon atoms. For example, alcohol ethoxylate compounds for use in the wetting agents of the present invention may each independently have structure represented by Formula I:

$$R\text{—}O\text{—}(CH_2CH_2O)_n\text{—}H \qquad (I)$$

wherein R is a ($C_1$-$C_{12}$) alkyl group and n is an integer in the range of 1 to 100. In some embodiments, R may be a ($C_8$-$C_{12}$) alkyl group, or may be a ($C_8$-$C_{10}$) alkyl group. Similarly, in some embodiments, n is an integer in the range of 10-50, or in the range of 15-30, or in the range of 20-25. In some embodiments, the one or more alcohol ethoxylate compounds are straight chain hydrophobes.

In at least some embodiments, the sheeting agent includes at least two different alcohol ethoxylate compounds each having structure represented by Formula I. That is, the R and/or n variables of Formula I, or both, may be different in the two or more different alcohol ethoxylate compounds present in the sheeting agent. For example, the sheeting agent in some embodiments may include a first alcohol ethoxylate compound in which R is a ($C_8$-$C_{10}$) alkyl group, and a second alcohol ethoxylate compound in which R is a ($C_{10}$-$C_{12}$) alkyl group. In at least some embodiments, the sheeting agent does not include any alcohol ethoxylate compounds that include an alkyl group that has more than 12 carbon atoms. In some embodiments, the sheeting agent includes only alcohol ethoxylate compounds that include an alkyl group that has 12 or fewer carbon atoms.

In some embodiments where, for example, the sheeting agent includes at least two different alcohol ethoxylate compounds, the ratio of the different alcohol ethoxylate compounds can be varied to achieve the desired characteristics of the final composition. For example, in some embodiments including a first alcohol ethoxylate compound and a second alcohol ethoxylate compound, the ratio of weight-percent first alcohol ethoxylate compound to weight-percent second compound may be in the range of about 1:1 to about 10:1 or more. For example, in some embodiments, the sheeting agent can include in the range of about 50 weight percent or more of the first compound, and in the range of about 50 weight percent or less of the second compound, and/or in the range of about 75 weight percent or more of the first compound, and in the range of about 25 weight percent or less of the second compound, and/or in the range of about 85 weight percent or more of the first compound, and in the range of about 15 weight percent or less of the second compound. Similarly, range of mole ratio of the first compound to the second compound may be about 1:1 to about 10:1, and in some embodiments, in the range of about 3:1 to about 9:1.

In some embodiments, the alcohol ethoxylates used in the sheeting agent can be chosen such that they have certain characteristics, for example, are environmentally friendly, are suitable for use in food service industries, and/or the like. For example, the particular alcohol ethoxylates used in the sheeting agent may meet environmental or food service regulatory requirements, for example, biodegradability requirements.

Some specific examples of suitable sheeting agents that may be used include an alcohol ethoxylate combination including a first alcohol ethoxylate wherein R is a $C_{10}$ alkyl group and n is 21 (i.e. 21 moles ethylene oxide) and a second alcohol ethoxylate wherein R is a $C_{12}$ alkyl group and again, n is 21 (i.e. 21 moles ethylene oxide). Such a combination can be referred to as an alcohol ethoxylate $C_{10\text{-}12}$, 21 moles EO. In some particular embodiments, the sheeting agent may include in the range of about 85 wt % or more of the $C_{10}$ alcohol ethoxylate and about 15 wt % or less of the $C_{12}$ alcohol ethoxylate. For example, the sheeting agent may include in the range of about 90 wt. % of the $C_{10}$ alcohol ethoxylate and about 10 wt % of the $C_{12}$ alcohol ethoxylate. One example of such an alcohol ethoxylate mixture is commercially available from Sasol as NOVEL II 1012-21.

The sheeting agent component can comprise a very broad range of weight percent of the entire composition, depending upon the desired properties. For example, in some embodiments, when the sheeting agent component is included in a wetting agent that is formulated as part of an antimicrobial composition, the amount of sheeting agent may be lower than when the wetting agent is not formulated as part of an antimicrobial composition. In some embodiments, the sheeting agent can be present in the composition from about 0.1 to about 10 wt % of the total composition. In other embodiments, the sheeting agent can be present at from about 0.2 to about 5 wt % of the total composition. For some diluted or use solutions, for example, aqueous use solutions, the sheeting agent can be present at from about 5 to about 250 ppm of the total use solution, about 50 to about 150 ppm of the total use solution, or form about 60 to 100 ppm of the total use solution. It is to be understood that all values and ranges between these values and ranges are encompassed by the present invention.

Defoaming Agent

In some aspects, the wetting agent compositions can also include a defoaming agent. The defoaming agent is present at amount effective for reducing the stability of foam that may be created by the alcohol ethoxylate sheeting agent in an aqueous solution. The defoaming agent can also contribute to the sheeting performance of the compositions of the present invention. Any of a broad variety of suitable defoamers may be used, for example, any of a broad variety of nonionic ethylene oxide (EO) containing surfactants. Many nonionic ethylene oxide derivative surfactants are water soluble and have cloud points below the intended use temperature of the wetting agent composition, and therefore may be useful defoaming agents.

While not wishing to be bound by theory, it is believed that suitable nonionic EO containing surfactants are hydrophilic and water soluble at relatively low temperatures, for example, temperatures below the temperatures at which the wetting agent will be used. It is theorized that the EO component forms hydrogen bonds with the water molecules, thereby solubilizing the surfactant. However, as the temperature is increased, these hydrogen bonds are weakened, and the EO containing surfactant becomes less soluble, or insoluble in water. At some point, as the temperature is increased, the cloud point is reached, at which point the surfactant goes out of solution, and functions as a defoamer. The surfactant can therefore act to defoam the sheeting agent component when used at temperatures at or above this cloud point.

Some examples of ethylene oxide derivative surfactants that may be used as defoamers include polyoxyethylene-polyoxypropylene block copolymers, alcohol alkoxylates, low molecular weight EO containing surfactants, or the like, or derivatives thereof. Some examples of polyoxyethylene-polyoxypropylene block copolymers include those having the following formulae:

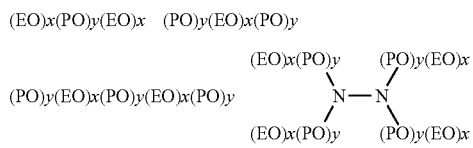

-continued

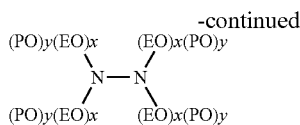

wherein EO represents an ethylene oxide group, PO represents a propylene oxide group, and x and y reflect the average molecular proportion of each alkylene oxide monomer in the overall block copolymer composition. In some embodiments, x is in the range of about 10 to about 130, y is in the range of about 15 to about 70, and x plus y is in the range of about 25 to about 200. It should be understood that each x and y in a molecule can be different. In some embodiments, the total polyoxyethylene component of the block copolymer can be in the range of at least about 20 mol-% of the block copolymer and in some embodiments, in the range of at least about 30 mol-% of the block copolymer. In some embodiments, the material can have a molecular weight greater than about 400, and in some embodiments, greater than about 500. For example, in some embodiments, the material can have a molecular weight in the range of about 500 to about 7000 or more, or in the range of about 950 to about 4000 or more, or in the range of about 1000 to about 3100 or more, or in the range of about 2100 to about 6700 or more.

Although the exemplary polyoxyethylene-polyoxypropylene block copolymer structures provided above have 3-8 blocks, it should be appreciated that the nonionic block copolymer surfactants can include more or less than 3 or 8 blocks. In addition, the nonionic block copolymer surfactants can include additional repeating units such as butylene oxide repeating units. Furthermore, the nonionic block copolymer surfactants that can be used according to the invention can be characterized heteric polyoxyethylene-polyoxypropylene block copolymers. Some examples of suitable block copolymer surfactants include commercial products such as PLURONIC® and TETRONIC® surfactants, commercially available from BASF. For example, PLURONIC® 25-R2 is one example of a useful block copolymer surfactant commercially available from BASF.

The defoamer component can comprise a very broad range of weight percent of the entire composition, depending upon the desired properties. For example, in some embodiments, when the defoamer component is included in a wetting agent that is formulated as part of an antimicrobial composition, the amount of defoamer component may be lower than when the wetting agent is not formulated as part of an antimicrobial composition. For example, for concentrated embodiments, the defoamer component can comprise in the range of 0.1 to about 10 wt % of the total composition, in some embodiments in the range of about 0.2 to about 5 wt % of the total composition, in some embodiments in the range of about 20 to about 50 wt % of the total composition, and in some embodiments in the range of about 40 to about 90 wt % of the total composition.

For some diluted or use solutions, the defoamer component can comprise in the range of 5 to about 60 ppm of the total use solution, in some embodiments in the range of about 50 to about 150 ppm of the total use solution, in some embodiments in the range of about 100 to about 250 ppm of the total use solution, and in some embodiments in the range of about 200 to about 500 ppm of the use solution.

The amount of defoaming agent present in the composition can also be dependent upon the amount of sheeting agent present in the composition. For example, less sheeting agent present in the composition may provide for the use of less defoamer component. In some example embodiments, the ratio of weight-percent sheeting agent component to weight-percent defoamer component may be in the range of about 1:5 to about 5:1, or in the range of about 1:3 to about 3:1. The ratio of sheeting agent component to defoamer component may be dependent on the properties of either and/or both actual components used, and these ratios may vary from the example ranges given to achieve the desired defoaming effect.

Association Disruption Agent

In some aspects, the wetting agent compositions can also include an association disruption agent. In some embodiments, the wetting agent compositions include one or more of an association disruption agent. Association disruption agents suitable for use in the compositions of the present invention include surfactants that are capable of interrupting the association of the other active agents, e.g., sheeting and defoaming agents, included in the wetting agents of the present invention.

In some embodiments, the association disruption agents included in the wetting agent compositions of the present invention reduce the contact angle of the wetting agent compositions. For example, in some embodiments, the association disruption agents reduce the contact angle of the wetting agent compositions by about 5°, about 10°, or by about 15°. Without wishing to be bound by any particular theory, it is thought that the lower the contact angle, the more a composition will induce sheeting. That is, compositions with lower contact angles will form droplets on a substrate with a larger surface area than compositions with higher contact angles. The increased surface area results in a faster drying time, with fewer spots formed on the substrate.

A variety of association disruption agents can be used in the wetting agent compositions of the present invention. In some embodiments, the association disruption agent includes an alcohol alkoxylate. In some embodiments, the alcohol alkoxylate includes a polyoxyethylene-polyoxypropylene copolymer surfactant (an "alcohol EO/PO surfactant"). The alcohol EO/PO surfactant can include a compact alcohol EO/PO surfactant where the EO and PO groups are in small block form, or random form. In other embodiments, the alcohol alkoxylate includes an ethylene oxide, a propylene oxide, a butylene oxide, a pentalene oxide, a hexylene oxide, a heptalene oxide, an octalene oxide, a nonalene oxide, a decylene oxide, and mixtures thereof. Exemplary commercially available association disruption agents include, but are not limited to, Genapol EP-2454® (commercially available from Clariant), Plurafac LF-221® (commercially available from BASF), Plurafac LF-500® (commercially available from BASF), and Dehypon® LS-54 (commercially available from Cognis).

In some embodiments, the wetting agent compositions of the present invention include at least one association disruption agent. In other embodiments, the wetting agent compositions of the present invention include at least two, at least three or at least four association disruption agents.

The association disruption agent(s) can comprise a very broad range of weight percent of the entire composition, depending upon the desired properties. For example, in some embodiments, when the association agent(s) is included in a wetting agent that is formulated as part of an antimicrobial composition, the amount of association agent(s) may be lower than when the wetting agent is not formulated as part of an antimicrobial composition. The association disruption agents can be present in the wetting agent compositions at between about 0.1 wt % to about 25 wt %. In some embodiments, the association disruption agent is present in the wetting agent composition at between about 1 wt % to about 20 wt %. In still yet other embodiments, the association disruption agent is present in the wetting agent composition at about 15 wt %.

In some embodiments the ratio of the sheeting agent, defoaming agent, and association disruption agent is selected so as to maximize the draining/drying time of the wetting agent compositions of the present invention. In some embodiments, the ratio of sheeting agent to defoaming agent to association disrupting agent is from about 1:1.5:30 to about 1:2:1. In some embodiments, the ratio of sheeting agent to defoaming agent to association disrupting agent is about 1:1.6:6.8. It is to be understood that all values and ranges between these values and ranges are encompassed by the present invention.

Additional Ingredients

The wetting agent compositions of the present invention may also optionally include a number of additional additives and/or functional materials. The additional ingredients can be included as part of the wetting agent composition itself. In other embodiments, the additional ingredients can be provided as a separate component in a composition which also includes the wetting agent composition of the present invention. Suitable additional ingredients include, but are not limited to, carriers, chelating/sequestering agents, bleaches and/or bleach activators, sanitizers and/or anti-microbial agents, activators, detergent builder or fillers, anti-redeposition agents, optical brighteners, dyes, odorants or perfumes, preservatives, stabilizers, processing aids, corrosion inhibitors, fillers, solidifiers, hardening agent, solubility modifiers, pH adjusting agents, humectants, hydrotropes, water treatment polymers and/or phosphonates, functional polydimethylsiloxones, or the like, or any other suitable additive, or mixtures or combinations thereof.

Carriers

In some embodiments, the compositions of the present invention are formulated as liquid compositions. Carriers can be included in such liquid formulations. Any carrier suitable for use in a wetting agent composition can be used in the present invention. For example, in some embodiments the compositions include water as a carrier.

In some embodiments, liquid compositions according to the present invention will contain no more than about 98 wt % water and typically no more than about 90 wt %. In other embodiments, liquid compositions will contain at least 50 wt % water, or at least 60 wt % water as a carrier.

Hydrotropes

In some embodiments, the compositions of the present invention can include a hydrotrope. The hydrotrope may be used to aid in maintaining the solubility of sheeting or wetting agents. Hydrotropes can also be used to modify the aqueous solution creating increased solubility for the organic material. In some embodiments, hydrotropes are low molecular weight aromatic sulfonate materials such as xylene sulfonates, dialkyldiphenyl oxide sulfonate materials, and cumene sulfonates.

A hydrotrope or combination of hydrotropes can be present in the compositions at an amount of from between about 1 wt % to about 50 wt %. In other embodiments, a hydrotrope or combination of hydrotropes can be present at about 10 wt % to about 30 wt % of the composition.

Anti-Microbial Agents

The wetting agent can optionally include an antimicrobial agent. The antimicrobial agent can be provided in a variety of ways. For example, in some embodiments, the antimicrobial agent is included as part of the wetting agent composition. In other embodiments, the antimicrobial agent can be included as a separate component of a composition including the wetting agent composition, e.g., as a separate component in a composition used in aseptic packaging/filling.

Antimicrobial agents are chemical compositions that can be used in a functional material to prevent microbial contamination and deterioration of material systems, surfaces, etc. Generally, these materials fall in specific classes including phenolics, halogen compounds, quaternary ammonium compounds, metal derivatives, amines, alkanol amines, nitro derivatives, analides, organosulfur and sulfur-nitrogen compounds and miscellaneous compounds.

In some embodiments, antimicrobial agents suitable for use with the wetting agent compositions of the present invention include percarboxylic acid compositions, and/or mixtures of diesters. For example, in some embodiments the antimicrobial agent included is at least one of peracetic acid, peroctanoic acid, and mixtures and derivatives thereof. In other embodiments, the antimicrobial agent may be a two solvent antimicrobial composition such as the composition disclosed in U.S. Pat. No. 6,927,237, the entire contents of which are hereby incorporated by reference.

In other embodiments, the antimicrobial agent may include compositions of mono- or diester dicarboxylates. Suitable mono- or diester dicarboxylates include mono- or dimethyl, mono- or diethyl, mono- or dipropyl (n- or iso), or mono- or dibutyl esters (n-, sec, or tert), or amyl esters (n-, sec-, iso-, or tert-) of malonic, succinic, glutaric, adipic, or sebacic acids, or mixtures thereof. Mixed esters (e.g., monomethyl/monoethyl, or monopropyl/monoethyl) can also be employed. Preferred mono- or diester dicarboxylates are commercially available and soluble in water or another carrier at concentrations effective for antimicrobial activity. Preferred mono- or diester dicarboxylates are toxic to microbes but do not exhibit unacceptable toxicity to humans under formulation or use conditions. Exemplary compositions including mono- or diester dicarboxylates are disclosed in U.S. Pat. No. 7,060,301, the entire contents of which are hereby incorporated by reference.

It should also be understood that active oxygen compounds, e.g., peroxygen compounds, such as those discussed in the bleaching agents section, may also act as antimicrobial agents, and can provide sanitizing activity. In some embodiments, the ability of the active oxygen compound to act as an antimicrobial agent reduces the need for additional antimicrobial agents within the composition. For example, percarbonate and percarboxylic acid compositions have been demonstrated to provide excellent antimicrobial action. Suitable percarboxylic compounds for use in the present invention include, but are not limited to, peracetic acid, peroctanoic acid, or a perester. In other embodiments, the percarboxylic acid composition is a short, medium or long chain percarboxylic acid, or combinations thereof.

Exemplary peroxygen compounds suitable for use in the compositions and methods of the present invention include, but are not limited to, hydrogen peroxide and its adducts such as sodium percarbonate and urea peroxide, sodium persulfate, sodium perborate, or the corresponding lithium, potassium, barium, calcium, or magnesium salts.

The given antimicrobial agent, depending on chemical composition and concentration, may simply limit further proliferation of numbers of the microbe or may destroy all or a portion of the microbial population. The terms "microbes" and "microorganisms" typically refer primarily to bacteria, virus, yeast, spores, and fungus microorganisms. In use, the antimicrobial agents are typically formed into a solid functional material that when diluted and dispensed, optionally, for example, using an aqueous stream forms an aqueous disinfectant or sanitizer composition that can be contacted with a variety of surfaces resulting in prevention of growth or the killing of a portion of the microbial population. A three log reduction of the microbial population results in a sanitizer composition. The antimicrobial agent can be encapsulated, for example, to improve its stability.

Some examples of common antimicrobial agents include phenolic antimicrobials such as pentachlorophenol, orthophenylphenol, a chloro-p-benzylphenol, p-chloro-m-xylenol. Halogen containing antibacterial agents include sodium trichloroisocyanurate, sodium dichloro isocyanate (anhydrous or dihydrate), iodine-poly(vinylpyrrolidinone) complexes, bromine compounds such as 2-bromo-2-nitropropane-1,3-diol, and quaternary antimicrobial agents such as benzalkonium chloride, didecyldimethyl ammonium chloride, choline diiodochloride, tetramethyl phosphonium tribromide. Other antimicrobial compositions such as hexahydro-1,3,5-tris(2-hydroxyethyl)-s-triazine, dithiocarbamates such as sodium dimethyldithiocarbamate, and a variety of other materials are known in the art for their antimicrobial properties. In some embodiments, the cleaning composition comprises sanitizing agent in an amount effective to provide a desired level of sanitizing. In some embodiments, an antimicrobial component, can be included in the range of up to about 75% by wt. of the composition, up to about 20 wt. %, in the range of about 1.0 wt % to about 20 wt %, in the range of about 5 wt % to about 10 wt %, in the range of about 0.01 to about 1.0 wt. %, or in the range of 0.05 to 0.05 wt % of the composition.

Chelating/Sequestering Agents

The wetting agent may optionally include one or more chelating/sequestering agent as an additional ingredient. A chelating/sequestering agent may include, for example an aminocarboxylic acid, a condensed phosphate, a phosphonate, a polyacrylate, and mixtures and derivatives thereof. In general, a chelating agent is a molecule capable of coordinating (i.e., binding) the metal ions commonly found in natural water to prevent the metal ions from interfering with the action of the other ingredients of a wetting agent or other cleaning composition. The chelating/sequestering agent may also function as a threshold agent when included in an effective amount. In some embodiments, the wetting agent compositions can include in the range of up to about 70 wt. %, or in the range of about 0.1 to about 60 wt. %, or about 0.1 to about 5.0 wt. %, of a chelating/sequestering agent. In some embodiments, the compositions of the invention include less than about 1.0 wt %, or less than about 0.5 wt % of a chelating/sequestering agent.

The composition may include a phosphonate such as 1-hydroxyethane-1,1-diphosphonic acid $CH_3C(OH)[PO(OH)_2]_2$; aminotri(methylenephosphonic acid) $N[CH_2\ PO(OH)_2]_3$; aminotri(methylenephosphonate), sodium salt

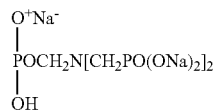

2-hydroxyethyliminobis(methylenephosphonic acid) $HOCH_2\ CH_2\ N[CH_2\ PO(OH)_2]_2$; diethylenetriaminepenta (methylenephosphonic acid) $(HO)_2\ POCH_2\ N[CH_2\ CH_2\ N[CH_2\ PO(OH)_2]_2]_2$; diethylenetriaminepenta(methylenephosphonate), sodium salt $C_9H_{(28-x)}\ N_3\ Na_xO_{15}P_5$ (x=7); hexamethylenediamine(tetramethylenephosphonate), potassium salt $C_{10}H_{(28-x)}N_2K_xO_{12}P_4$ (x=6); bis(hexamethylene)triamine(pentamethylenephosphonic acid) $(HO_2)POCH_2N[(CH_2)_6N[CH_2\ PO(OH)_2]_2]_2$; and phosphorus acid $H_3PO_3$. In some embodiments, a phosphonate combination such as ATMP and DTPMP may be used. A neutralized or alkaline phosphonate, or a combination of the phosphonate with an alkali source prior to being added into the mixture such that there is little or no heat or gas generated by a neutralization reaction when the phosphonate is added can be used.

Some examples of polymeric polycarboxylates suitable for use as sequestering agents include those having a pendant carboxylate ($-CO_2$) groups and include, for example, polyacrylic acid, maleic/olefin copolymer, acrylic/maleic copolymer, polymethacrylic acid, acrylic acid-methacrylic acid copolymers, hydrolyzed polyacrylamide, hydrolyzed polymethacrylamide, hydrolyzed polyamide-methacrylamide copolymers, hydrolyzed polyacrylonitrile, hydrolyzed polymethacrylonitrile, hydrolyzed acrylonitrile-methacrylonitrile copolymers, and the like.

For a further discussion of chelating agents/sequestrants, see Kirk-Othmer, Encyclopedia of Chemical Technology, Third Edition, volume 5, pages 339-366 and volume 23, pages 319-320, the disclosure of which is incorporated by reference herein.

Bleaching Agents

The wetting agent can optionally include a bleaching agent. Bleaching agents can be used for lightening or whitening a substrate, and can include bleaching compounds capable of liberating an active halogen species, such as $Cl_2$, $Br_2$, $-OCl^-$ and/or $-OBr^-$, or the like, under conditions typically encountered during the cleansing process. Suitable bleaching agents for use can include, for example, chlorine-containing compounds such as a chlorine, a hypochlorite, chloramines, of the like. Some examples of halogen-releasing compounds include the alkali metal dichloroisocyanurates, chlorinated trisodium phosphate, the alkali metal hypochlorites, monochloramine and dichloroamine, and the like. Encapsulated chlorine sources may also be used to enhance the stability of the chlorine source in the composition.

A bleaching agent may also include an agent containing or acting as a source of active oxygen. The active oxygen compound acts to provide a source of active oxygen, for example, may release active oxygen in aqueous solutions. An active oxygen compound can be inorganic or organic, or can be a mixture thereof. Some examples of active oxygen compound include peroxygen compounds, or peroxygen compound adducts. Some examples of active oxygen compounds or sources include hydrogen peroxide, perborates, sodium carbonate peroxyhydrate, phosphate peroxyhydrates, potassium permonosulfate, and sodium perborate mono and tetrahydrate, with and without activators such as tetraacetylethylene diamine, and the like. A wetting agent composition may include a minor but effective amount of a bleaching agent, for example, in some embodiments, in the range of up to about 10 wt. %, and in some embodiments, in the range of about 0.1 to about 6 wt. %.

Activators

In some embodiments, the antimicrobial activity or bleaching activity of the wetting agent can be enhanced by the addition of a material which, when the composition is placed in use, reacts with the active oxygen to form an activated component. For example, in some embodiments, a peracid or a peracid salt is formed. For example, in some embodiments, tetraacetylethylene diamine can be included within the composition to react with the active oxygen and form a peracid or a peracid salt that acts as an antimicrobial agent. Other examples of active oxygen activators include transition metals and their compounds, compounds that contain a carboxylic, nitrile, or ester moiety, or other such compounds known in the art. In an embodiment, the activator includes tetraacetylethylene diamine; transition metal; compound that includes carboxylic, nitrile, amine, or ester moiety; or mixtures thereof.

In some embodiments, an activator component can include in the range of up to about 75% by wt. of the composition, in some embodiments, in the range of about 0.01 to about 20% by wt, or in some embodiments, in the range of about 0.05 to 10% by wt of the composition. In some embodiments, an activator for an active oxygen compound combines with the active oxygen to form an antimicrobial agent.

Builders or Fillers

The wetting agent can optionally include a minor but effective amount of one or more of a filler which does not necessarily perform as a rinse and/or cleaning agent per se, but may cooperate with a rinse agent to enhance the overall capacity of the composition. Some examples of suitable fillers may include sodium sulfate, sodium chloride, starch, sugars, $C_1$-$C_{10}$ alkylene glycols such as propylene glycol, and the like. In some embodiments, a filler can be included in an amount in the range of up to about 20 wt. %, and in some embodiments, in the range of about 1-15 wt. %.

Anti-Redeposition Agents

The wetting agent composition can optionally include an anti-redeposition agent capable of facilitating sustained suspension of soils in a rinse solution and preventing removed soils from being redeposited onto the substrate being rinsed. Some examples of suitable anti-redeposition agents can include fatty acid amides, fluorocarbon surfactants, complex phosphate esters, styrene maleic anhydride copolymers, and cellulosic derivatives such as hydroxyethyl cellulose, hydroxypropyl cellulose, and the like. A wetting agent composition may include up to about 10 wt. %, and in some embodiments, in the range of about 1 to about 5 wt. %, of an anti-redeposition agent.

Dyes/Odorants

Various dyes, odorants including perfumes, and other aesthetic enhancing agents may also be included in the wetting agent. Dyes may be included to alter the appearance of the composition, as for example, FD&C Blue 1 (Sigma Chemical), FD&C Yellow 5 (Sigma Chemical), Direct Blue 86 (Miles), Fastusol Blue (Mobay Chemical Corp.), Acid Orange 7 (American Cyanamid), Basic Violet 10 (Sandoz), Acid Yellow 23 (GAF), Acid Yellow 17 (Sigma Chemical), Sap Green (Keyston Analine and Chemical), Metanil Yellow (Keystone Analine and Chemical), Acid Blue 9 (Hilton Davis), Sandolan Blue/Acid Blue 182 (Sandoz), Hisol Fast Red (Capitol Color and Chemical), Fluorescein (Capitol Color and Chemical), Acid Green 25 (Ciba-Geigy), and the like.

Fragrances or perfumes that may be included in the compositions include, for example, terpenoids such as citronellol, aldehydes such as amyl cinnamaldehyde, a jasmine such as C1S-jasmine or jasmal, vanillin, and the like.

Hardening/Solidification Agents/Solubility Modifiers

In some embodiments, the compositions of the invention are formulated as aqueous liquid wetting agent compositions. In other embodiments, the compositions of the invention are solid wetting agent compositions.

A wetting agent may include an effective amount of a hardening agent, as for example, an amide such stearic monoethanolamide or lauric diethanolamide, or an alkylamide, and the like; a solid polyethylene glycol, urea, or a solid EO/PO block copolymer, and the like; starches that have been made water-soluble through an acid or alkaline treatment process; various inorganics that impart solidifying properties to a heated composition upon cooling, and the like. Such compounds may also vary the solubility of the composition in an aqueous medium during use such that the wetting agent and/or other active ingredients may be dispensed from the solid composition over an extended period of time. The composition may include a hardening agent in an amount in the range of up to about 50 wt %, or in some embodiments, in the range of about 20 wt % to about 40 wt %, or about 5 to about 15 wt-%.

Functional Polydimethylsiloxones

The composition can also optionally include one or more functional polydimethylsiloxones. For example, in some embodiments, a polyalkylene oxide-modified polydimethylsiloxane, nonionic surfactant or a polybetaine-modified polysiloxane amphoteric surfactant can be employed as an additive. Both, in some embodiments, are linear polysiloxane copolymers to which polyethers or polybetaines have been grafted through a hydrosilation reaction. Some examples of specific siloxane surfactants are known as SILWET® surfactants available from Union Carbide or ABIL® polyether or polybetaine polysiloxane copolymers available from Goldschmidt Chemical Corp., and described in U.S. Pat. No. 4,654,161 which patent is incorporated herein by reference. In some embodiments, the particular siloxanes used can be described as having, e.g., low surface tension, high wetting ability and excellent lubricity. For example, these surfactants are said to be among the few capable of wetting polytetrafluoroethylene surfaces. The siloxane surfactant employed as an additive can be used alone or in combination with a fluorochemical surfactant. In some embodiments, the fluorochemical surfactant employed as an additive optionally in combination with a silane, can be, for example, a nonionic fluorohydrocarbon, for example, fluorinated alkyl polyoxyethylene ethanols, fluorinated alkyl alkoxylate and fluorinated alkyl esters.

Further description of such functional polydimethylsiloxones and/or fluorochemical surfactants are described in U.S. Pat. Nos. 5,880,088; 5,880,089; and 5,603,776, all of which patents are incorporated herein by reference. We have found, for example, that the use of certain polysiloxane copolymers in a mixture with hydrocarbon surfactants provide excellent wetting agents on plasticware. We have also found that the combination of certain silicone polysiloxane copolymers and fluorocarbon surfactants with conventional hydrocarbon surfactants also provide excellent wetting agents on plasticware. This combination has been found to be better than the individual components except with certain polyalkylene oxide-modified polydimethylsiloxanes and polybetaine polysiloxane copolymers, where the effectiveness is about equivalent. Therefore, some embodiments encompass the polysiloxane copolymers alone and the combination with the fluorocarbon surfactant can involve polyether polysiloxanes, the nonionic siloxane surfactants. The amphoteric siloxane surfactants, the polybetaine polysiloxane copolymers may be employed alone as the additive in the wetting agents to provide the same results.

In some embodiments, the composition may include functional polydimethylsiloxones in an amount in the range of up to about 10 wt-%. For example, some embodiments may include in the range of about 0.1 to 10 wt-% of a polyalkylene oxide-modified polydimethylsiloxane or a polybetaine-modified polysiloxane, optionally in combination with about 0.1 to 10 wt-% of a fluorinated hydrocarbon nonionic surfactant.

Humectant

The composition can also optionally include one or more humectant. A humectant is a substance having an affinity for water. The humectant can be provided in an amount sufficient to aid in reducing the visibility of a film on the substrate surface. The visibility of a film on substrate surface is a particular concern when the rinse water contains in excess of 200 ppm total dissolved solids. Accordingly, in some embodiments, the humectant is provided in an amount sufficient to reduce the visibility of a film on a substrate surface when the rinse water contains in excess of 200 ppm total dissolved solids compared to a rinse agent composition not containing the humectant. The terms "water solids filming" or "filming" refer to the presence of a visible, continuous layer of matter on a substrate surface that gives the appearance that the substrate surface is not clean.

Some example humectants that can be used include those materials that contain greater than 5 wt. % water (based on dry humectant) equilibrated at 50% relative humidity and room temperature. Exemplary humectants that can be used include glycerin, propylene glycol, sorbitol, alkyl polyglycosides, polybetaine polysiloxanes, and mixtures thereof. In some embodiments, the wetting agent composition can include humectant in an amount in the range of up to about 75% based on the total composition, and in some embodiments, in the range of about 5 wt. % to about 75 wt. % based on the weight of the composition. In some embodiments, where humectant is present, the weight ratio of the humectant to the sheeting agent can be in the range of about 1:3 or greater, and in some embodiments, in the range of about 5:1 and about 1:3.

Other Ingredients

A wide variety of other ingredients useful in providing the particular composition being formulated to include desired properties or functionality may also be included. For example, the wetting agent may include other active ingredients, such as pH buffers, cleaning enzyme, carriers, processing aids, solvents for liquid formulations, or others, and the like.

Additionally, the wetting agent can be formulated such that during use in aqueous operations, for example in aqueous cleaning operations, the rinse water will have a desired pH. For example, compositions designed for use in rinsing may be formulated such that during use in aqueous rinsing operation the rinse water will have a pH in the range of about 3 to about 5, or in the range of about 5 to about 9. Liquid product formulations in some embodiments have a (10% dilution) pH in the range of about 2 to about 4, or in the range of about 4 to about 9. Techniques for controlling pH at recommended usage levels include the use of buffers, alkali, acids, etc., and are well known to those skilled in the art. One example of a suitable acid for controlling pH includes citric acid. In some embodiments, no additional acid is added to the wetting agent compositions.

Methods of Use

The wetting agent compositions of the invention can be used for a variety of domestic or industrial applications. The compositions can be applied in a variety of areas including kitchens, bathrooms, factories, hospitals, dental offices, pharmaceutical plants or co-packers, and food plants or co-packers, and can be applied to a variety of hard or soft surfaces having smooth, irregular or porous topography. Suitable hard surfaces include, for example, architectural surfaces (e.g., floors, walls, windows, sinks, tables, counters and signs); eating utensils; hard-surface medical or surgical instruments and devices; and hard-surface packaging. Such hard surfaces can be made from a variety of materials including, for example, ceramic, metal, glass, wood or hard plastic. Suitable soft surfaces include, for example paper, filter media, hospital and surgical linens and garments, soft-surface medical or surgical instruments and devices, and soft-surface packaging. Such soft surfaces can be made from a variety of materials including, for example, paper, fiber, woven or nonwoven fabric, soft plastics and elastomers.

The wetting agent compositions of the invention can be used in a variety of applications. For example, in some embodiments, the compositions of the present invention can be formulated for use in aseptic packaging and filing operations. In other embodiments, the wetting agent may be particularly formulated for use in warewashing machines. There are two general types of rinse cycles in commercial warewashing machines. A first type of rinse cycle can be referred to as a hot water sanitizing rinse cycle because of the use of generally hot rinse water (about 180° F.). A second type of rinse cycle can be referred to as a chemical sanitizing rinse cycle and it uses generally lower temperature rinse water (about 120° F.).

In some embodiments, it is believed that the wetting agent composition of the invention can be used in a high solids containing water environment in order to reduce the appearance of a visible film caused by the level of dissolved solids provided in the water. In general, high solids containing water is considered to be water having a total dissolved solids (TDS) content in excess of 200 ppm. In certain localities, the service water contains a total dissolved solids content in excess of 400 ppm, and even in excess of 800 ppm. The applications where the presence of a visible film after washing a substrate is a particular problem includes the restaurant or warewashing industry, the car wash industry, and the general cleaning of hard surfaces.

Exemplary articles in the warewashing industry that can be treated with a wetting agent according to the invention include plastics, dishware, cups, glasses, flatware, and cookware. For the purposes of this invention, the terms "dish" and "ware" are used in the broadest sense to refer to various types of articles used in the preparation, serving, consumption, and disposal of food stuffs including pots, pans, trays, pitchers, bowls, plates, saucers, cups, glasses, forks, knives, spoons, spatulas, and other glass, metal, ceramic, plastic composite articles commonly available in the institutional or household kitchen or dining room. In general, these types of articles can be referred to as food or beverage contacting articles because they have surfaces which are provided for contacting food and/or beverage. When used in these warewashing applications, the wetting agent should provide effective sheeting action and low foaming properties. In addition to having the desirable properties described above, it may also be useful for the wetting agent to be biodegradable, environmentally friendly, and generally nontoxic. A wetting agent of this type may be described as being "food grade".

The wetting agent compositions may also be applied to surfaces and objects other than ware, including, but not limited to, medical and dental instruments, and hard surfaces such as vehicle surfaces. The compositions may also be used as wetting agents in a variety of applications for a variety of surfaces, e.g., as wetting agents for aseptic packaging/filling of plastic containers.

In some embodiments, the wetting agents of the present invention can be used in the manufacture of beverage, food, and pharmaceutical materials including fruit juice, dairy products, malt beverages, soybean-based products, yoghurts, baby foods, bottled water products, teas, cough medicines, drugs, and soft drinks. The wetting agents can be incorporated into compositions used in aseptic packaging and filling. The wetting agents help aid in the dissolution of certain highly insoluble antimicrobial agents used in such processes. Further, when included in antimicrobial compositions used in packaging, the wetting agents of the present invention increase the coverage of the compositions on the contacted substrate. This increased coverage has been found to increase the sterilization of the substrate. Without wishing to be bound by any particular theory, it is also thought that the wetting agents of the present invention substantially reduce the adsorption of chemicals into plastic surfaces due to the faster draining/drying. Further, the wetting agents of the present invention are rinsed off surfaces relatively easily.

The wetting agents of the present invention can be included in compositions used to sanitize, disinfect, act as a sporicide for, or sterilize bottles, pumps, lines, tanks and mixing equipment used in the manufacture of such beverages. The wetting agents can also be included in antimicrobial compositions used in aseptic, cold filling operations in which the interior of the food, beverage, or pharmaceutical container is sanitized or sterilized prior to filling. In such operations, a container is contacted with the antimicrobial composition including the wetting agents, typically using a spray, or dipping, or filling device to intimately contact the inside of then container with the composition, for sufficient period of time to reduce microorganism populations within the container. The container is then emptied of the amount of antimicrobial composition used. After emptying, the container can then be rinsed with potable water or sterilized water and again emptied; however, this is not a required step. After rinsing, the container is then filled with the beverage, food, or pharmaceutical. The container is then sealed, capped or closed and then packed for shipment for ultimate sale. The sealed container can be autoclaved or retorted for added microorganism kill.

In other embodiments, the wetting agents of the present invention can be used in cold aseptic filling techniques. In such techniques, metallic, aluminum or steel cans can be filled, glass bottles or containers can be filled or plastic (PET or PBT or PEN) bottles, and the like can be filled using cold aseptic filling techniques. Wetting agents of the present invention can be included in antimicrobial compositions used to sanitize the interior of beverage containers prior to filling with the carbonated beverage. Typical carbonated beverages in this application include cola beverage, fruit beverages, ginger ale beverages, root beer beverages, iced tea beverages which may be non-carbonated, and other common beverages considered soft drinks. The wetting agents of the invention can be included in compositions used to sanitize both the tanks, lines, pumps, and other equipment used for the manufacture and storage of the soft drink material and also used in the bottling or containers for the beverages.

EXAMPLES

The present invention is more particularly described in the following examples that are intended as illustrations only. Unless otherwise noted, all parts, percentages, and ratios reported in the following examples are on a weight basis, and all reagents used in the examples were obtained, or are available, from the chemical suppliers described below, or may be synthesized by conventional techniques.

Example 1

A test was run to measure the sheeting abilities of an exemplary wetting agent of the present invention (Composition A) compared to a comparative wetting agent (Comparative Composition B), when used with an antimicrobial agent. Comparative composition B included a mixture of 5-8 wt % fatty alcohol ethoxylates, 2-5 wt % di-propylene glycol ethers, 16-19 wt % alkylethoxy-propoxylates, and 1-2 wt % organic acids, as the active ingredients. Composition A included a wetting agent formed using the components in the weight percents shown in the table below.

TABLE 1

| Composition A | | |
|---|---|---|
| Ingredient | Type of Agent | Wt % |
| Fatty Alcohol Alkoxylate | Association Disruption Agent | 0.84 |
| Alkoxylated Alcohol | Association Disruption Agent | 0.4416 |
| Alkoxylated Alcohol | Association Disruption Agent | 0.84 |
| EO/PO Block Polymer | Defoaming Agent | 0.4416 |
| Ethoxylated Alcohol | Sheeting Agent | 0.3192 |

Composition A also included 0.48% of a hydrotrope.

Each of the above compositions was used to formulate the test compositions. The test compositions included two antimicrobial compositions. The first antimicrobial composition was a peracetic acid product, and the second antimicrobial agent was a low solubility mixture of diesters (dimethyl ester of hexanedioc acid, and dimethyl sebacate). The first antimicrobial agent included 4200 ppm of active agent, and the second antimicrobial agent included 1250 ppm of active agent. The table below shows the components of the four compositions tested.

TABLE 2

| | Test Compositions | | | |
|---|---|---|---|---|
| Ingredient | 1 (wt %) | 2 (wt %) | 3 (wt %) | 4 (wt %) |
| Antimicrobial composition 1 (peracetic acid composition) | 2.89 | 2.89 | 2.89 | 2.89 |
| Antimicrobial composition 2 (diester mixture) | 0.1 | 0.1 | 0.1 | 0.1 |
| Water | 96.39 | 96.86 | 96.41 | 96.86 |
| Composition A | 0 | 0 | 0.595 | 0.149 |
| Comparative Composition B | 0.617 | 0.154 | 0 | 0 |

Test compositions 1 and 3 were formulated to have 200 ppm active wetting agent concentration. Test compositions 2 and 4 each had 50 ppm active wetting agent concentration. To make these compositions, antimicrobial composition 1 and 2 were first mixed together. The water and either Composition A or Comparative Composition B were then added after the initial mixing.

To perform the sheeting test, PET slides were etched 1 centimeter from the bottom and placed into 100 mls of one of the above test solutions maintained at about 140° F. in a 150 ml beaker. When the slides were removed (after about 30 seconds), they were placed in a drying rack. The time it took for the solution to pass below the etched line was recorded. The results are shown in the table below.

TABLE 3

| Test Composition | Time (minutes) | Observations |
|---|---|---|
| 1 | 6:17 | Small pinhole sheeting |
| 2 | 6:04 | Incomplete sheeting |
| 3 | 4:28 | Complete sheeting |
| 4 | 4:11 | Incomplete sheeting |

As can be seen from these results, the test compositions that included the exemplary wetting agent of the present invention (test compositions 3 and 4) had much shorter draining/drying times. On average the draining/drying time for the compositions using the exemplary wetting agent of the present invention was about 30% faster.

The test was run again using 300 mls of each test composition in a 400 ml beaker. This was due to the fact that when using 100 mls in a 150 ml beaker, only about half of the slide was submerged. Using the test with 300 ml resulted in the slide being completely covered. The same test solutions described above were prepared, and the test method was identical (other than the amount of solution used). However, for this test, the slides were etched at 3 centimeters from the bottom of the slide. Also, the draining/drying time of both the front and the back of each slide was also measured in this test. The results are shown in the table below.

TABLE 4

| Test Composition | Time (minutes) | Observations |
| --- | --- | --- |
| 1 | Front: 2:42<br>Back/Total: 5:23 | Small pinhole sheeting |
| 2 | Front: 2:45<br>Back/Total: 4:10 | Initial shedding/hourglass with large pinholes |
| 3 | Front: 1:33<br>Back/Total: 2:16 | Complete sheeting |
| 4 | Front: 1:42<br>Back/Total: 2:37 | Initial shedding/hourglass with large pinholes |

As can be seen from these results, the test compositions that included the exemplary wetting agent of the present invention (test compositions 3 and 4) had much shorter draining/drying times. The test solution including 200 ppm active of Composition A (test composition 3) had the shortest draining/drying time, and was also the only solution to give complete sheeting. The draining/drying time of this composition was more than a minute faster than the draining/drying time of the test composition that included 200 ppm of Comparative Composition B.

Example 2

A test was run to compare the contact angles of test solutions that include compositions of the present invention and similar test compositions with other comparative wetting agents. For this test, the test solutions were not heated above room temperature. The test solutions are also shown in the table below.

TABLE 5

| | Test Compositions | | | |
| --- | --- | --- | --- | --- |
| Ingredient | 1 (wt %) | 2 (wt %) | 3 (wt %) | 4 (wt %) |
| Antimicrobial composition 1 (peracetic acid composition) | 2.89 | 2.89 | 2.89 | 2.89 |
| Antimicrobial composition 2 (diester mixture) | 0.1 | 0.1 | 0.1 | 0.1 |
| Water | 96.39 | 96.86 | 96.41 | 96.86 |
| Composition A | 0 | 0 | 0.595 | 0.149 |
| Comparative Composition B | 0.617 | 0.154 | 0 | 0 |

Composition A, Comparative Composition B, antimicrobial composition 1, and antimicrobial composition 2 are the same as described in Example 1. The contact angle of these solutions was measured at room temperature on polyethylene terephthalate (PET) slides. After each of the compositions was prepared, the compositions were placed into an apparatus where a single drop of the composition was delivered to the PET slides. The deliverance of the drop to the substrate was recorded by a camera. The video captured by the camera was sent to a computer were the contact angle was be determined. The results of this test are shown in the table below.

TABLE 6

| Test Solution | Contact Angle | Average Contact Angle |
| --- | --- | --- |
| DI Water | 68.1<br>69.6<br>68.9 | 68.9 |
| Control (Neither Composition A or Comparative Composition B present) | 61.1<br>65.9<br>60.0 | 62.4 |
| Test Solution 1 | 44.9<br>45.6<br>47.2 | 45.9 |
| Test Solution 2 | 51.1<br>52.1<br>52.9 | 52.0 |
| Test Solution 3 | 30.1<br>29.8<br>31.65 | 30.5 |
| Test Solution 4 | 47.5<br>44.6<br>46.6 | 46.3 |

These results are also shown in FIG. 1. As can be seen from these results, the test compositions that included the exemplary wetting agent of the present invention (Test Solutions 3 and 4) had much lower contact angles than the test solutions that included the conventional wetting agent (Test Solutions 1 and 2). On average, the test solution that included 200 ppm of active Composition A (Test Solution 3) had a contact angle that was 15° lower than that of the test solution that included Comparative Composition B at the same concentration. Overall, it was found that inclusion of an exemplary wetting agent of the present invention led to lower contact angles than those found using conventional wetting agents at the same concentrations.

Example 3

A test was run to measure the sheeting abilities and draining/drying times of an exemplary wetting agent of the present invention compared to a comparative wetting agent, when used with an antimicrobial agent. For this test, the same wetting agent compositions as described in Example 1 were tested. That is, Comparative Composition B included a mixture of 5-8 wt % fatty alcohol ethoxylates, 2-5 wt % dipropylene glycol ethers, 16-19 wt % alkylethoxy-propoxylates, and 1-2 wt % organic acids, as the active ingredients. The formula for Composition A included an exemplary wetting agent composition of the present invention shown in the table below.

TABLE 7

| Composition A | | |
| --- | --- | --- |
| Ingredient | Type of Agent | Wt % |
| Fatty Alcohol Alkoxylate | Association Disruption Agent | 0.84 |
| Alkoxylated Alcohol | Association Disruption Agent | 0.4416 |
| Alkoxylated Alcohol | Association Disruption Agent | 0.84 |
| EO/PO Block Polymer | Defoaming Agent | 0.4416 |
| Ethoxylated Alcohol | Sheeting Agent | 0.3192 |

Composition A also included 0.48 wt % of a hydrotrope.

Each of these wetting agent compositions were tested at 50 ppm active and 200 ppm active agent concentrations. The antimicrobial agent used included 4200 ppm peracetic acid as the active antimicrobial agent. The test compositions are shown in the table below.

TABLE 8

| | Test Compositions | | | |
|---|---|---|---|---|
| Ingredient | 1 (wt %) | 2 (wt %) | 3 (wt %) | 4 (wt %) |
| Antimicrobial composition 1 (peracetic acid composition) | 2.89 | 2.89 | 2.89 | 2.89 |
| Water | 96.49 | 96.96 | 96.51 | 96.96 |
| Composition A | 0 | 0 | 0.595 | 0.149 |
| Comparative Composition B | 0.617 | 0.154 | 0 | 0 |

To perform the sheeting test, PET slides were etched 3 centimeter from the bottom and placed into 300 mls of one of the above test solutions maintained at about 140° F. in a 400 ml beaker. When the slides were removed from the test solutions after about 30 seconds, they were placed in a drying rack. The time it took for the solution to pass below the etched line in the front, and the back (total time) was recorded. The results are shown in the table below.

TABLE 9

| Test Composition | Time (minutes) | Observations |
|---|---|---|
| 1 | Front: 1:48 Back/Total: 2:44 | Complete sheeting |
| 2 | Front: 2:16 Back/Total: 3:48 | Initial shedding/hourglass with large pinholes |
| 3 | Front: 1:28 Back/Total: 1:47 | Complete sheeting |
| 4 | Front: 1:32 Back/Total: 2:07 | Initial shedding/hourglass with large pinholes |

As can be seen from these results, although both test solutions containing 200 ppm active (Test Compositions 1 and 3) resulted in complete sheeting, the test composition including an exemplary wetting agent of the present invention (Test Composition 3) resulted in complete sheeting and draining/drying in a much short time period. At 200 ppm active wetting agent, Test Composition 3 led to complete draining/drying almost 1 minute faster than Test Composition 1 which included the comparative wetting agent.

The contact angle of these solutions was measured at room temperature on PET slides. After each of the compositions was prepared, the compositions were placed into an apparatus where a single drop of the composition was delivered to the PET slides. The deliverance of the drop to the substrate was recorded by a camera. The video captured by the camera was sent to a computer were the contact angle was be determined. The results of this test are shown in the table below.

TABLE 10

| Test Solution | Contact Angle | Average Contact Angle |
|---|---|---|
| DI Water | 68.1 69.6 68.9 | 68.9 |
| Control (Neither Composition A or Comparative Composition B present) | 61.1 65.9 60.0 | 62.4 |
| Test Solution 1 | 56.0 56.7 | 56.4 |
| Test Solution 2 | 52.0 55.2 56.0 | 54.4 |

TABLE 10-continued

| Test Solution | Contact Angle | Average Contact Angle |
|---|---|---|
| Test Solution 3 | 45.0 44.6 41.6 | 43.7 |
| Test Solution 4 | 49.2 47.8 48.9 | 48.6 |

Figure 2:
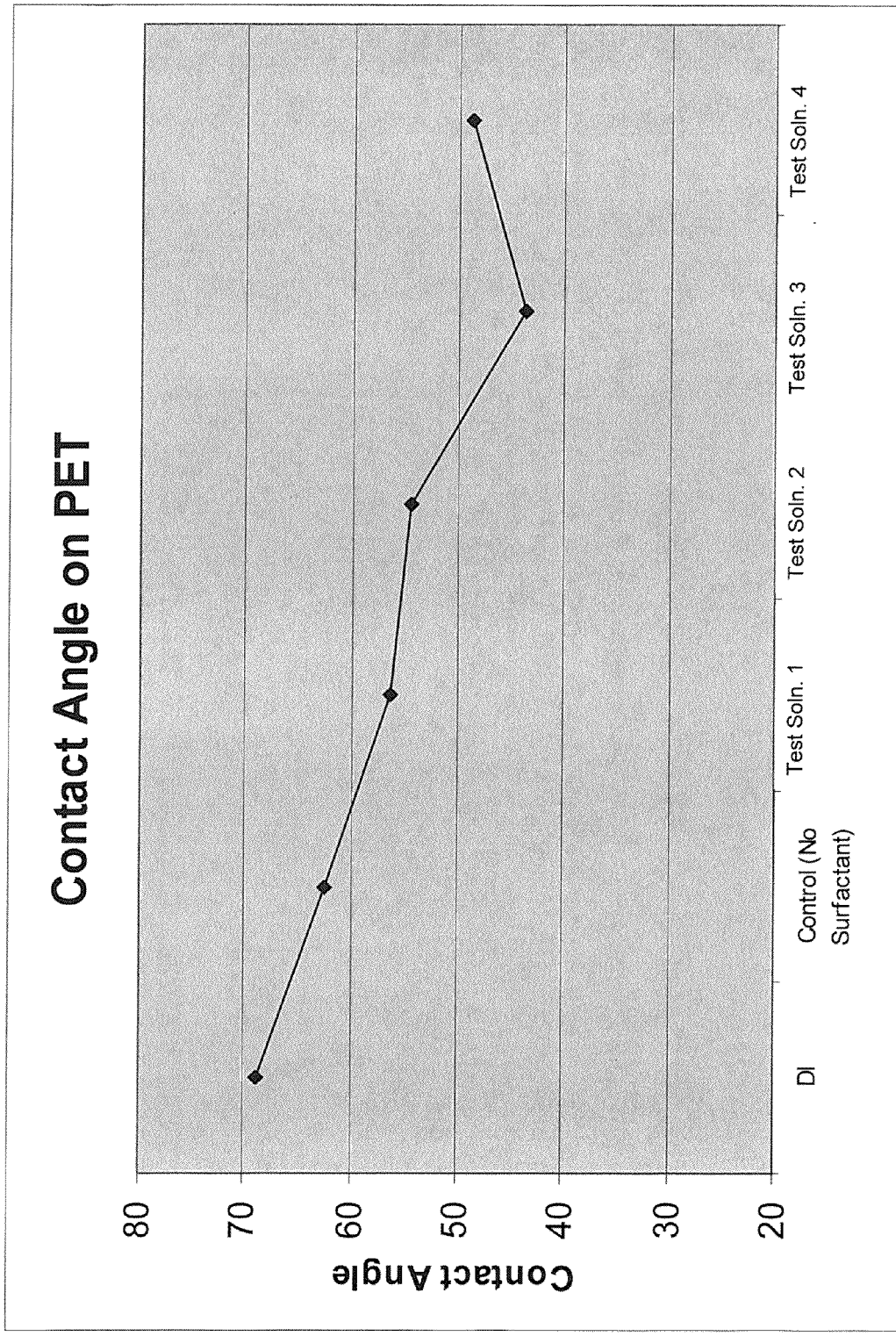
FIG. 2 is a graphical depiction of the average contact angle of various test solutions as described in Example 3.

These results are also graphically depicted in FIG. 2. As can be seen from these results, the test compositions that included an exemplary wetting agent of the present invention (Test Solutions 3 and 4) had lower contact angles than those solutions that included a conventional wetting agent. The composition that included a wetting agent of the present invention at 200 ppm (Test Solution 3) had a contact angle that was about 30% less than that of the equivalent composition with 200 ppm of a conventional wetting agent (Test Solution 1).

Example 4

Viscoelasticity Test

A study was performed to measure the viscoelasticity of exemplary wetting agent compositions of the present invention and comparative compositions. Without wishing to be bound by any particular theory, it is thought that the thin-film viscoelasticity of a solution is related to the overall sheeting, draining and drying of the solution on the substrates to which they are applied. It is thought that a certain elasticity is important for the liquid to generally hold the "sheets." However, too high a level of elasticity can hinder drainage and drying of the rinse aid from the substrate.

The viscoelasticity measurements for this study were taken using a Bohlin CVO 120 HR NF Rheometer. The measurements were taken for neat or high concentration solutions (in case the 100% material is a solid at room temperature) of individual surfactants, and combinations of surfactants. The measurements are measured in the linear viscoelastic range. The data plotted were G' and G" versus strain. G' is the elastic component of the complex modulus, and G" is the viscous component of the complex modulus. The association effect of the surfactant molecules was studied. The results of this study are shown in FIGS. 3A through 3G. In these figures, the x-axis depicts the strain. In this example, strain is a ratio of two lengths and has no units. It is defined by the formula shown below:

$$\text{Shear strain} = \delta u/h.$$

In these figures, the y-axis is shows units of pascal ("Pa"). The pascal is the SI derived unit of pressure, stress, Young's Modulus and tensile stress. It is a measure of force per unit area, i.e., equivalent to one newton per square meter.

As can be seen from these figures, an exemplary sheeting agent surfactant, Novel 1012 GB-21, had a large G' and G", which suggests a strong association effect. An exemplary defoaming agent surfactant tested, Pluronic® 25R2, had a large G", but a low G'. A 50/50 combination of these surfactants (FIG. 3C) showed a large G' and G", which showed a strong association effect that was not broken down by the mixing of the two surfactants.

Figure 3A:
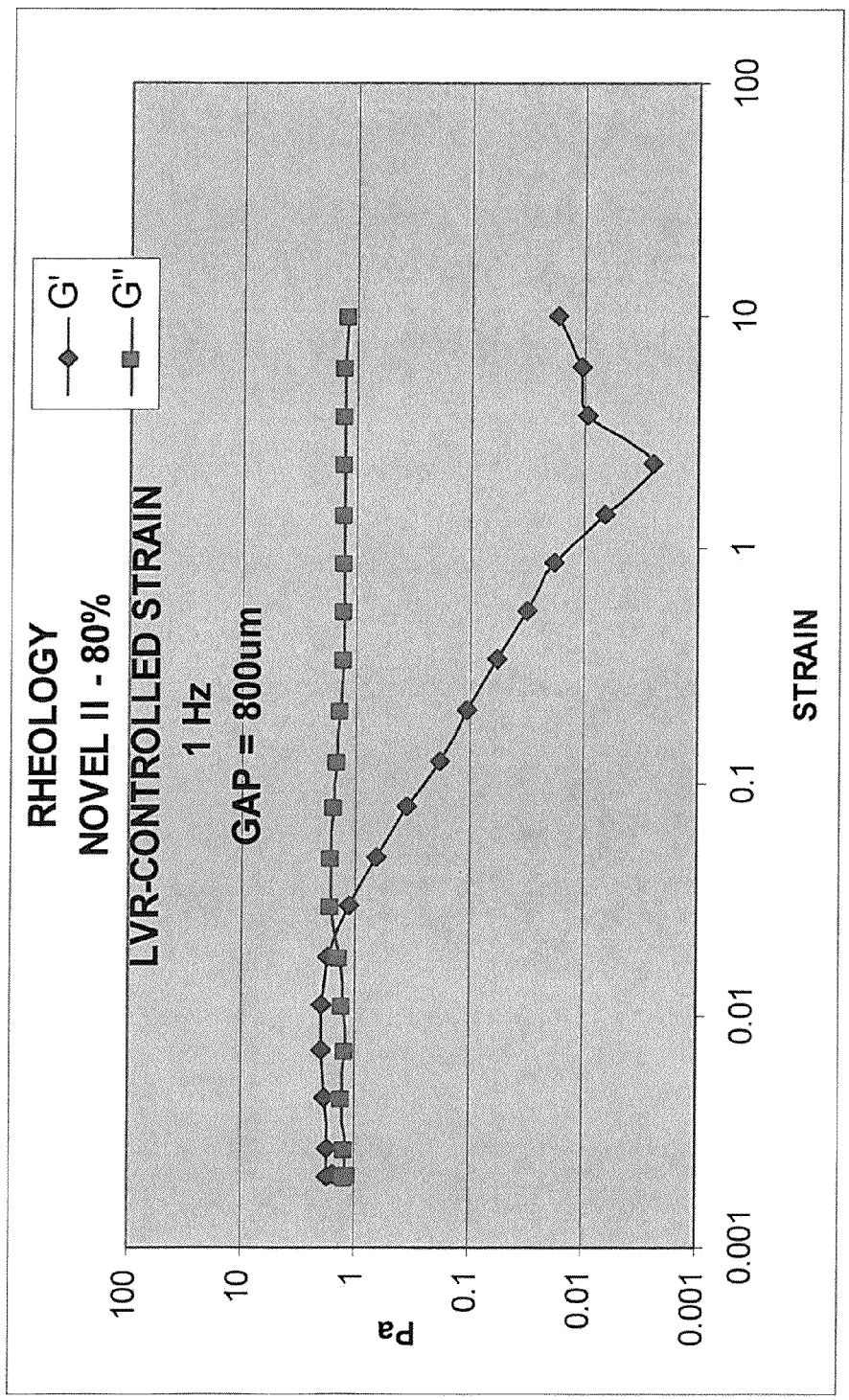
FIGS. 3a through 3f are graphical depictions of the G' and G" of exemplary sheeting agents, defoaming agents, and association disruption agents for use in the compositions of the present invention.
Figure 3B:
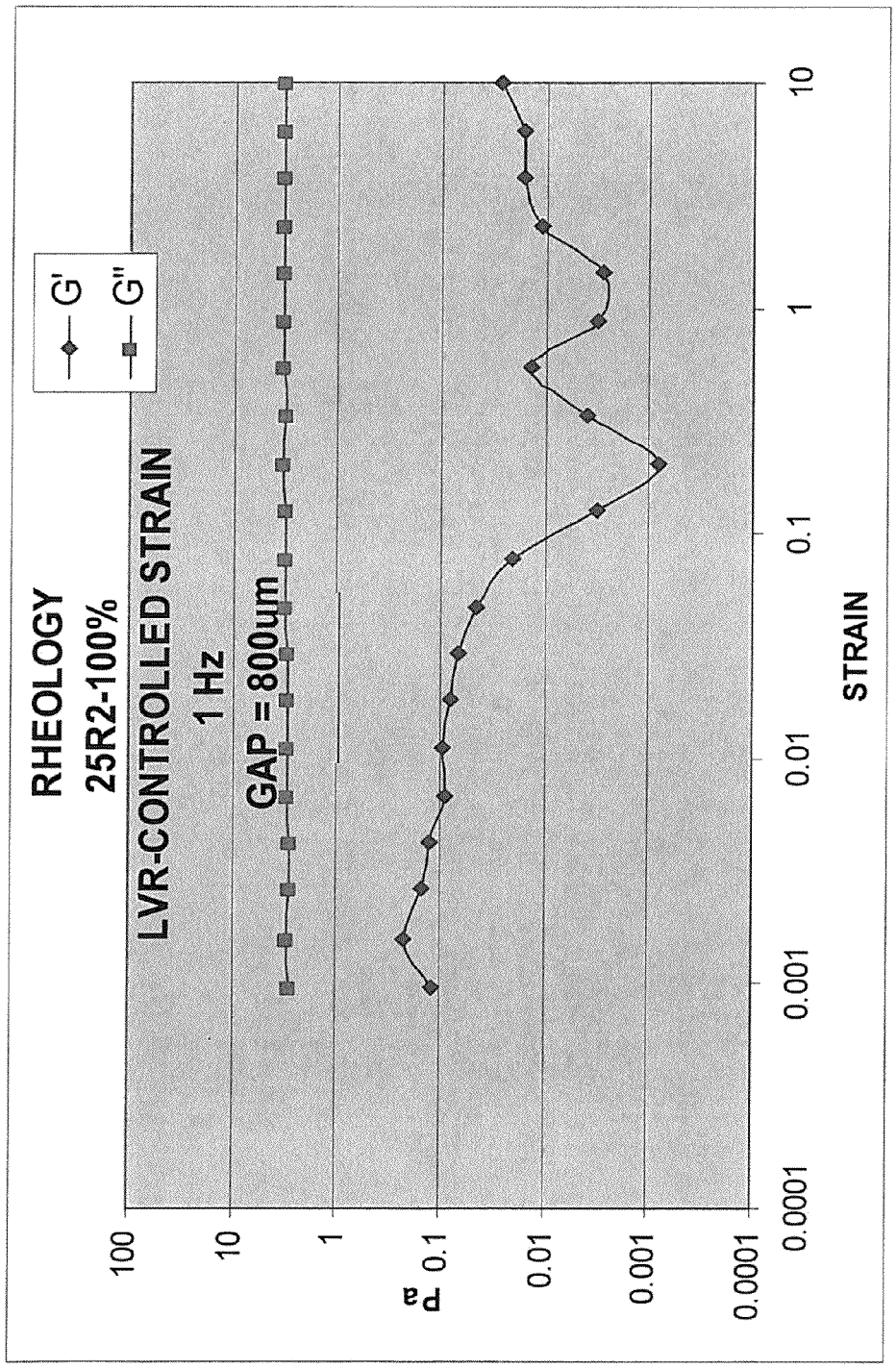
Figure 3C:
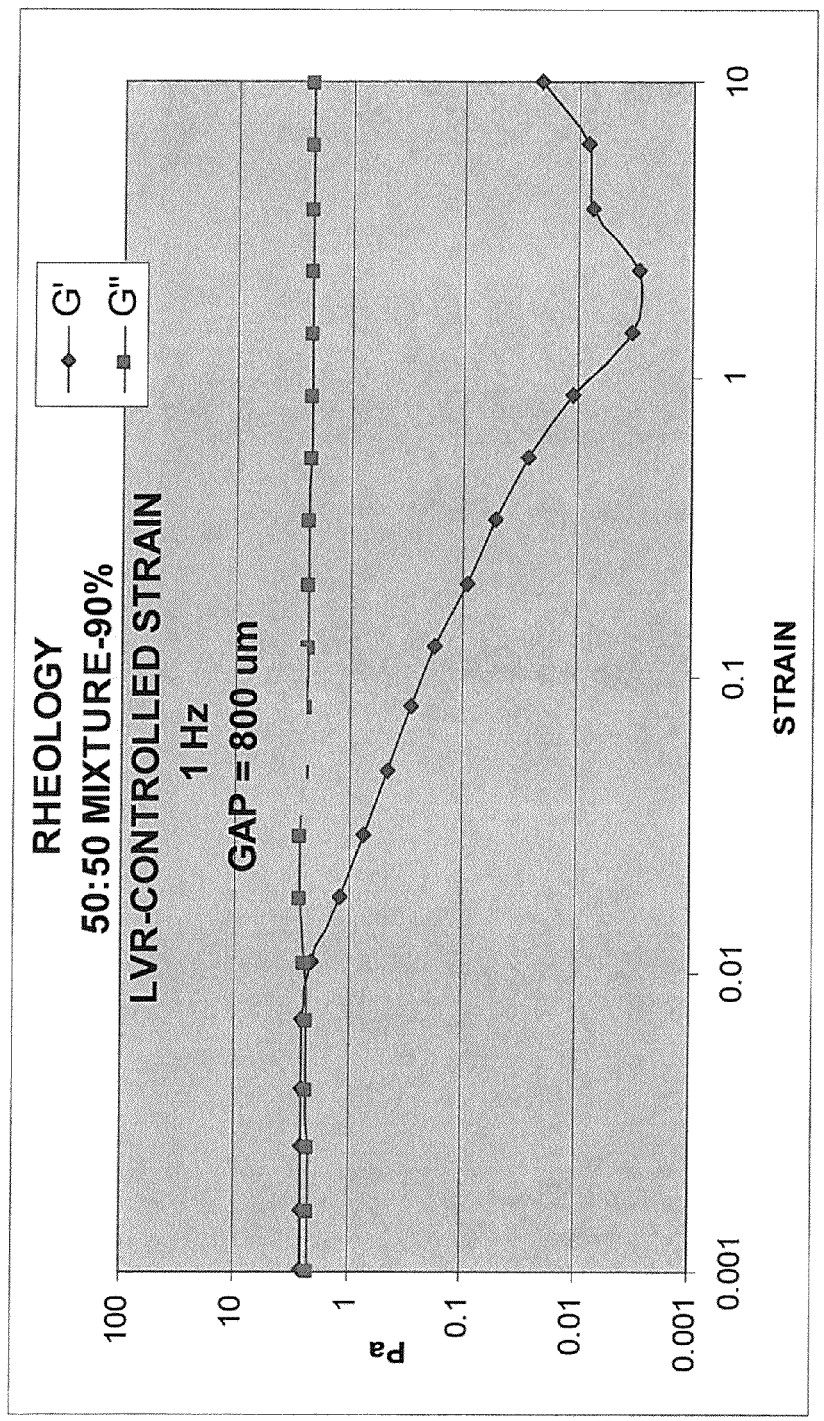
Figure 3D:
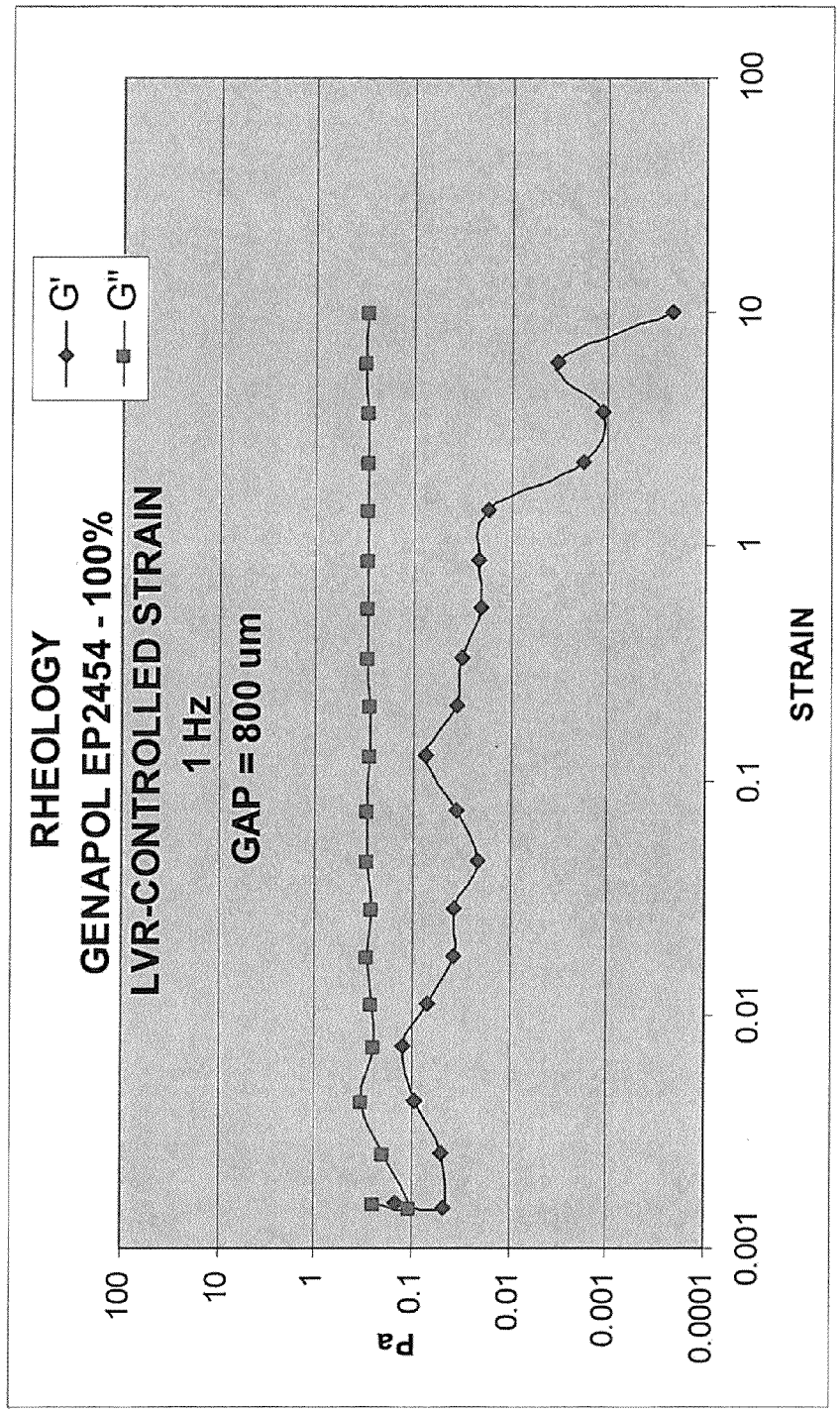
Figure 3E:
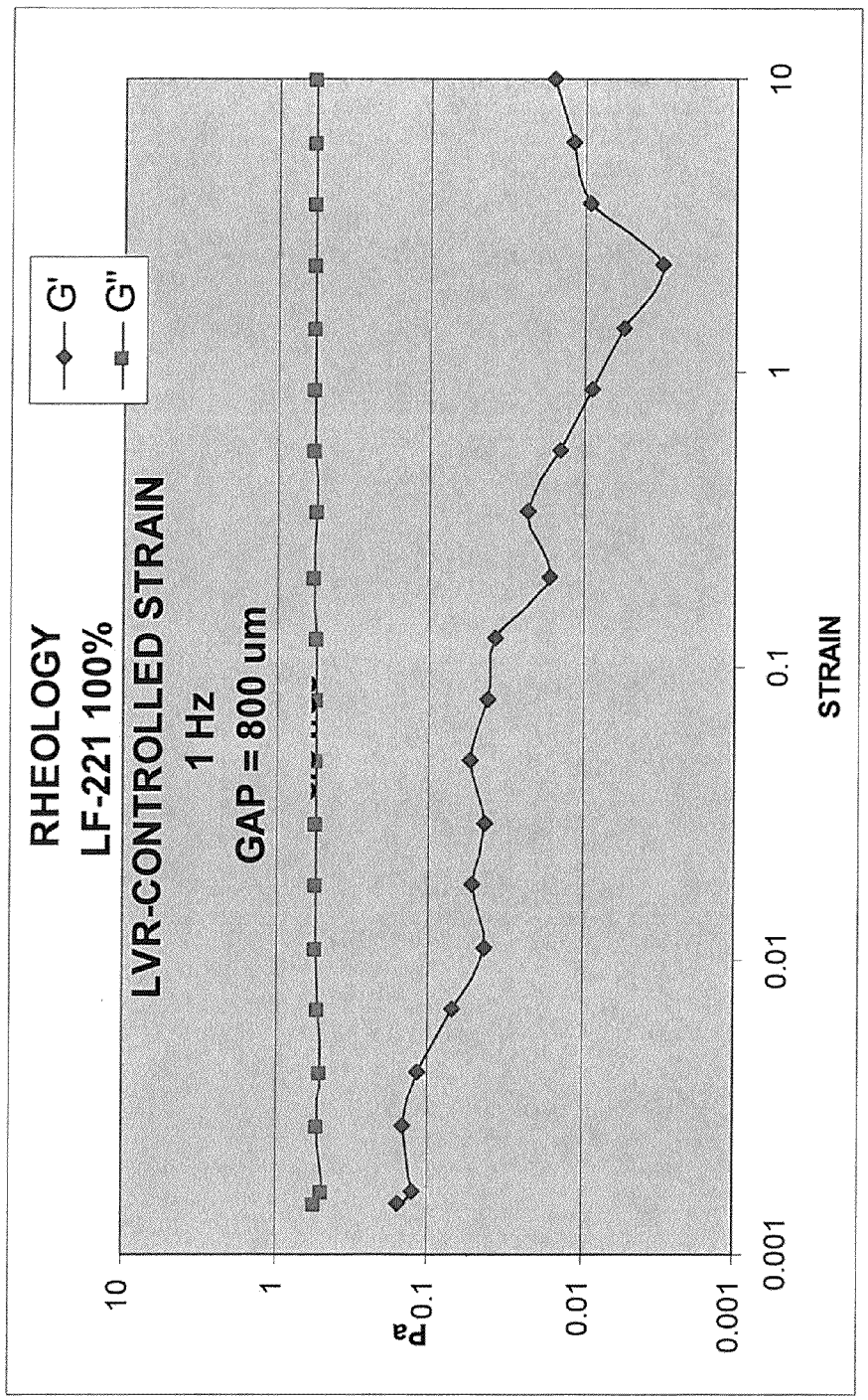
Figure 3F:
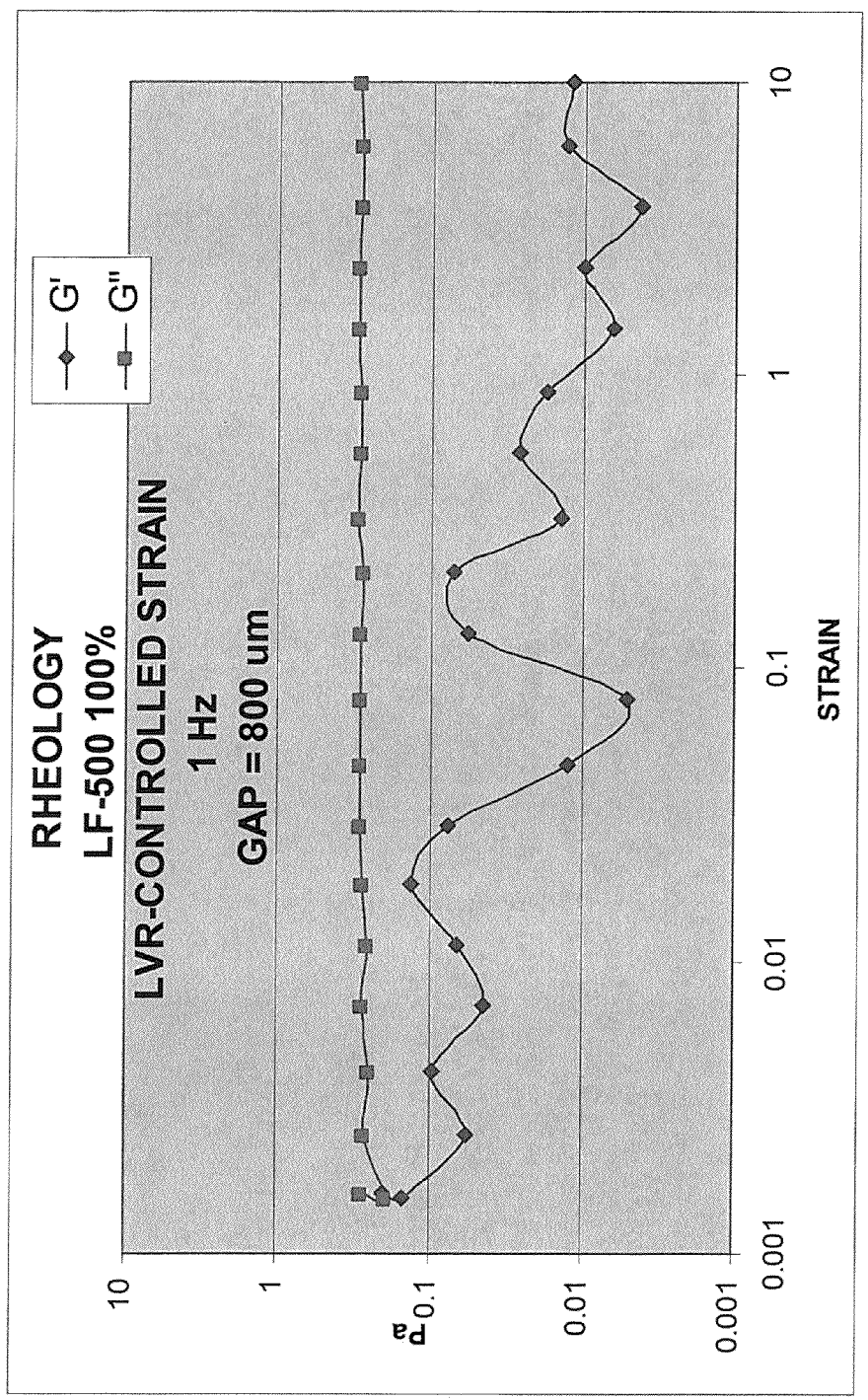

Association disruption type surfactants, for example, Genapol EP-2454®, Plurafac LF-221®, and Plurafac LF-500®, all had relatively low G' and G" (FIGS. 3D, 3E, and 3F). This was expected due to their non-associative nature.

Figure 3G:
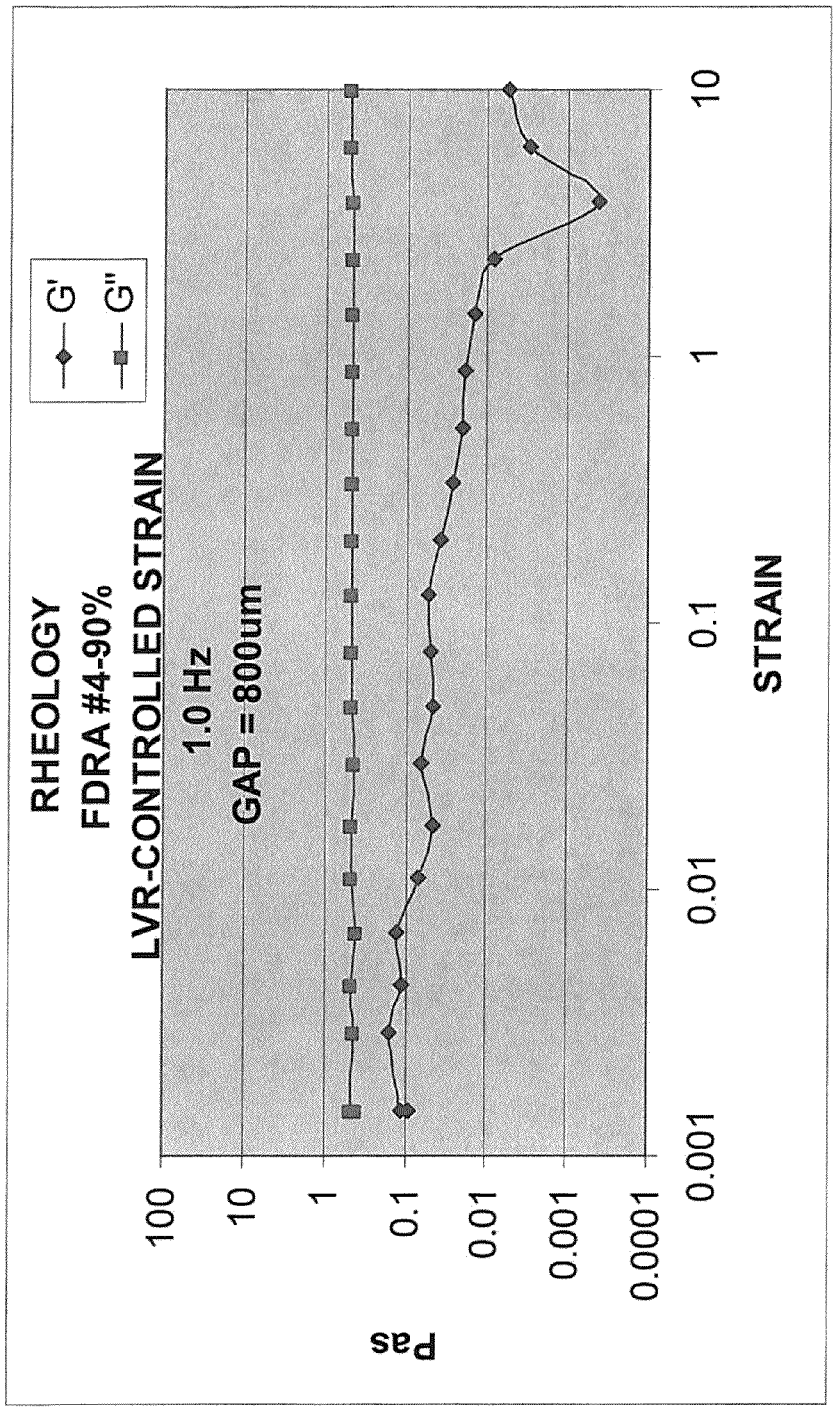
FIG. 3g is a graphical depiction of the G' and G" of an exemplary composition of the present invention.

However, a combination of all of the above types of surfactants, shown in FIG. 3G, had a very low G' and G" suggesting that the association disruption agent type surfactants disrupts the associations of the sheeting agent and defoaming agent type surfactants.

Example 5

Foaming Evaluation

A test was run to determine the foam profiles of several exemplary wetting agents according to the present invention. A Glewwe foam apparatus was used for this test. The following procedure was used. First, each formula was prepared and gently poured into a Glewwe cylinder. Samples tested contained 50 ppm of actives of the rinse aid additive or surfactant combination to be evaluated. A ruler was attached to the side of the cylinder, and the solution was level with the bottom of the ruler. The pump was turned on. Foam height was estimated by reading the average level of foaming according to the ruler. Foam height readings were taken versus time with a stopwatch or timer. The pump was turned off and height of the foam was recorded at various times. Food soil was added after one minute of run time. Each sample was tested at 140° F., at a pressure of 6.0 psi. The foam level was read after one minute of agitation and again after 5 minutes of agitation for a given amount of time. A stable foam remains for several minutes after agitation is stopped. Partially stable foam breaks slowly within a minute. Unstable foam breaks rapidly in less than 15 seconds. A desirable rinse aid should have unstable foam to no foam.

The table below shows the surfactants tested, and their corresponding class in this study.

TABLE 9

| Surfactant | Class |
| --- | --- |
| Genapol EP-2454 ® (commercially available from Clariant) | Association Disruption Agent |
| Plurafac LF-221 ® (commercially available from BASF) | Association Disruption Agent |
| Plurafac LF-500 ® (commercially available from BASF) | Association Disruption Agent |
| Neodol 45-13 ® | Sheeting Agent |
| Pluronic ® 25R2 (commercially available from BASF) | Defoaming Agent |
| Dehypon ® LS-54 (commercially available from Cognis) | Association Disruption Agent |
| Novel ® 1012GB-21 (commercially available from Sasol) | Sheeting Agent |

The results from the foaming test are shown in the table below.

TABLE 10

| Product | Ratio of Surfactant | After 1 min. (total) run time | | | After 5 min. (total) run time after addition of food soil | | |
| --- | --- | --- | --- | --- | --- | --- | --- |
| | | Initial | 15 Sec. | 1 Min. | Initial | 15 Sec. | 1 Min. |
| Genapol/LF-221/Neodol 45-13/25R2 | equal parts | 2 | 1 | ¼ | 6 | 5 | 4½ |
| Genapol/Dehypon/LF-221/LF-500 | equal parts | 0 | 0 | 0 | 3 | ¼ | ¼ |
| Genapol/LF-221/Neodol 45-13 | equal parts | 6 | 4½ | 2 | 11 | 10 | 8 |
| Neodol 45-13/LF-221/LF-500 | equal parts | 5 | 4½ | 2 | 10 | 9 | 8 |
| Neodol 45-13/LF-221/LF-500/Genapol | equal parts | 4 | 3 | ½ | 9 | 8 | 7 |
| Genapol/LF-221/Novel/25R2 | equal parts | Trace | 0 | 0 | 3 | ¼ | ¼ |
| Genapol/LF-221/Novel/(2)25R2 | 1/1/1/2 | 0 | 0 | 0 | 2½ | <⅛ | <⅛ |
| Genapol/LF-221/Novel/(3)25R2 | 1/1/1/3 | 0 | 0 | 0 | 2 | <⅛ | <⅛ |
| Genapol/Dehypon/LF-221/LF-500 | equal parts | 0 | 0 | 0 | 3 | ¼ | ¼ |
| Genapol/Dehypon/LF-221/LF-500/25R2 | equal parts | 0 | 0 | 0 | 2½ | ¼ | ¼ |
| Genapol/Dehypon/LF-221/LF-500/(2)25R2 | 1/1/1/1/2 | 0 | 0 | 0 | | | |
| Genapol/LF-221/Novel | equal parts | Trace | Trace | Trace | 6½ | 5½ | 2½ |
| Novel/LF-221/LF-500 | equal parts | Trace | 0 | 0 | 4½ | 2 | ½ |
| Novel/LF-221/LF-500/25R2 | equal parts | 0 | 0 | 0 | 3 | ¼ | ¼ |
| Novel/LF-221/LF-500/(2)25R2 | 1/1/1/2 | 0 | 0 | 0 | 2 | Trace | Trace |
| Novel/LF-221/LF-500/Genapol | equal parts | Trace | 0 | 0 | 4½ | 1 | ½ |
| Novel/LF-221/LF-500/Genapol/25R2 | equal parts | 0 | 0 | 0 | 2¾ | ¼ | ¼ |
| Novel/LF-221/LF-500/Genapol/(2)25R2 | 1/1/1/2 | 0 | 0 | 0 | 2¼ | ¼ | ¼ |

As can be seen from this table, Novel® 1012 GB-21 was superior to Neodol 45-13 as a sheeting agent type surfactant. All of the surfactant combinations tested that included the Neodol surfactant had an excess of foam. No combination of association disruption agent or defoaming agent was effective at defoaming the Neodol surfactant for a rinse aid application. It was also found that association disruption agents were not able to defoam the sheeting agents alone. Rather, a combination of defoaming agent, and association disruption agent was necessary to effectively defoam the sheeting agents tested.

Other Embodiments

It is to be understood that while the invention has been described in conjunction with the detailed description thereof, the foregoing description is intended to illustrate, and not limit the scope of the invention, which is defined by the scope of the appended claims. Other aspects, advantages, and modifications are within the scope of the following claims.

In addition, the contents of all patent publications discussed supra are incorporated in their entirety by this reference.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The invention claimed is:

1. A method for aseptic packaging of food, beverages or pharmaceuticals comprising:
   (a) contacting a package with a composition consisting essentially of a wetting agent, and an antimicrobial agent, wherein the wetting agent consists essentially of:
      (i) a sheeting agent, wherein the sheeting agent comprises at least one compound having the structure represented by formula I:

R—O—(CH$_2$CH$_2$O)$_n$—H wherein R is a (C$_1$-C$_{12}$) alkyl group, and n is an integer in the range of 1 to 100;
      (ii) a defoaming agent comprising a polyoxypropylene-polyoxyethylene block copolymer surfactant, wherein the weight percent ratio of sheeting agent to defoaming agent is between about 1:5 to about 5:1 in the composition;
      (iii) a first association disruption agent which is an alcohol alkoxylate EO/BO surfactant;
      (iv) a second association disruption agent which is a C$_{12}$-C$_{14}$ fatty alcohol EO/PO surfactant; and
      (v) an additional ingredient selected from the group consisting of a carrier, a hydrotrope, a chelating/sequestering agent, and combinations thereof;
   (b) filling the package with a substance selected from the group consisting of food, beverage, pharmaceutical, and combinations thereof; and
   (c) sealing the package.

2. The method of claim 1, wherein the step of contacting comprises applying the composition to the packaging for an amount of time sufficient to reduce a microorganism population present on the package.

3. The method of claim 2, wherein the composition is applied to the packaging for at least 3 seconds.

4. The method of claim 1, wherein the step of contacting comprises applying the composition to the packaging at a temperature of between about 0° C. and about 100° C.

5. The method of claim 1, wherein n is an integer in the range of 15 to 30.

6. The method of claim 1, wherein n is 21.

7. The method of claim 1, wherein the antimicrobial agent is selected from the group consisting of a peroxygen compound, a percarboxylic acid, a monoester of a dicarboxylic acid, a diester of a dicarboxylic acid, and mixtures thereof.

8. The method of claim 1, wherein the wetting agent is present in the composition at an amount of from about 20 ppm to about 2000 ppm.

9. The method of claim 1, wherein the method further comprises a rinse step between the step of contacting the package with the composition, and filling the package with a substance.

10. A wetting agent composition consisting essentially of:
    (a) a sheeting agent, wherein the sheeting agent comprises at least one compound having the structure represented by formula 1:

R—O—(CH2CH$_2$O)$_n$—H, wherein R is a (C$_1$-C$_{12}$) alkyl group, and n is an integer in the range of 1 to 100;
    (b) a defoaming agent comprising a polyoxypropylene-polyoxyethylene block copolymer surfactant, wherein the weight percent ratio of sheeting agent to defoaming agent is between about 1:5 to about 5:1 in the composition;
    (c-1) a first association disruption agent which is an alcohol alkoxylate EO/BO surfactant;
    (c-2) a second association disruption agent which is a C$_{12}$-C$_{14}$ fatty alcohol EO/PO surfactant; and
    (d) an additional ingredient selected from the group consisting of a carrier, a hydrotrope, a chelating/sequestering agent, and combinations thereof.

11. A composition consisting essentially of:
    (a) a wetting agent composition consisting essentially of:
       (i) a sheeting agent, wherein the sheeting agent comprises at least one compound having the structure represented by formula I:

R—O—(CH$_2$CH$_2$O)$_n$—H, wherein R is a (C$_1$-C$_{12}$) alkyl group, and n is an integer in the range of 1 to 100;
       (ii) a defoaming agent comprising a polyoxypropylene-polyoxyethylene block copolymer surfactant, wherein the weight percent ratio of sheeting agent to defoaming agent is between about 1:5 to about 5:1 in the composition;
       (iii) a first association disruption agent which is an alcohol alkoxylate EO/BO surfactant;
       (iv) a second association disruption agent which is a C$_{12}$-C$_{14}$ fatty alcohol EO/PO surfactant; and
       (v) an additional ingredient selected from the group consisting of a carrier, a hydrotrope, a chelating/sequestering agent, and combinations thereof; and
    (b) an antimicrobial agent.

12. A method for aseptic packaging comprising:
    (a) forming an aseptic packaging use solution comprising diluting a composition to a use concentration of between about 0.01 wt % to about 10 wt %, wherein the composition consists essentially of:
       (i) a wetting agent consisting essentially of:
          (a) a sheeting agent, wherein the sheeting agent comprises at least one compound having the structure represented by formula I:

R—O—(CH$_2$CH$_2$O)$_n$—H wherein R is a (C$_1$-C$_{12}$) alkyl group, and n is an integer in the range of 1 to 100;
          (b) a defoaming agent comprising a polyoxypropylenepolyoxyethylene block copolymer surfactant, wherein the weight percent ratio of sheeting agent to defoaming agent is between about 1:5 to about 5:1 in the composition;
          (c-1) a first association disruption agent which is an alcohol alkoxylate EO/BO surfactant; and
          (c-2) a second association disruption agent which is a C$_{12}$-C$_{14}$ fatty alcohol EO/PO surfactant;
       (ii) and an antimicrobial agent;
    (b) contacting a package with the aseptic packaging use solution;
    (c) filling the package with a substance selected from the group consisting of food, beverage, pharmaceutical, and combinations thereof; and
    (d) sealing the package.

13. The method of claim 12, wherein the sheeting agent is present at about 0.1 wt % to about 10 wt %.

14. The method of claim 12, wherein t s Se ting agent is present at about 0.2 wt % to about 5 wt %.

15. The method of claim 12, wherein the defoaming agent is present at about 0.1 wt % to about 10 wt %.

16. The method of claim 12, wherein the foaming agent is present at about 0.2 wt % to about 5 wt %.

17. The method of claim 12, wherein the one or more association disruption agent is present at between about 0.1 wt % to about 25 wt %.

18. The method of claim 12, wherein the disruption agent is present at between about 1 wt % to about 20 wt %.

19. The method of claim 12, wherein the antimicrobial agent is selected from the group consisting of a peroxygen compound, a percarboxylic acid, a monoester of a dicarboxylic acid, a diester of a dicarboxylic acid, and mixtures thereof.

* * * * *

UNITED STATES PATENT AND TRADEMARK OFFICE
CERTIFICATE OF CORRECTION

PATENT NO. : 8,567,161 B2  
APPLICATION NO. : 12/778711  
DATED : October 29, 2013  
INVENTOR(S) : Man et al.

Page 1 of 1

It is certified that error appears in the above-identified patent and that said Letters Patent is hereby corrected as shown below:

In the Claims:

Col. 27, Claim 10, Line 55:
DELETE after formula "1"
ADD after formula --I--

Col. 28, Claim 14, Line 54:
DELETE after wherein "t s Se ting"
ADD after wherein --the sheeting--

Col. 28, Claim 16, Line 58:
DELETE after the "foaming"
ADD after the --defoaming--

Signed and Sealed this  
Thirty-first Day of December, 2013

Margaret A. Focarino  
*Commissioner for Patents of the United States Patent and Trademark Office*